US005744442A

United States Patent [19]
Richards et al.

[11] Patent Number: 5,744,442
[45] Date of Patent: Apr. 28, 1998

[54] REGULATION OF CELLULAR INVASIVENESS

[75] Inventors: Carl D. Richards, Hamilton, Canada; Mohammed Shoyab, Seattle, Wash.; Jack Gauldie, Hamilton, Canada; Thomas Joseph Brown, Poulsbo, Wash.

[73] Assignees: Bristol Meyers Squibb Company, New York, N.Y.; McMaster University, Hamilton, Canada

[21] Appl. No.: 935,097

[22] Filed: Aug. 26, 1992

[51] Int. Cl.$^6$ .......................... A01N 37/18; C07K 14/475
[52] U.S. Cl. ................................. 514/2; 530/350
[58] Field of Search .................... 530/351, 350; 424/85.1; 514/2

[56] References Cited

U.S. PATENT DOCUMENTS 4,973,478  11/1990  Gauldie et al. ............... 424/85.4
5,202,116  4/1993  Brown .

FOREIGN PATENT DOCUMENTS 0 290 948 A2  11/1988  European Pat. Off. .

OTHER PUBLICATIONS

Bowman et al 1980 Textbook of Pharmacology 2$^{nd}$ Ed. Blockwell Scientific Publications Oxford p. 4.19.

T. Taga and t. Kishimot, "Cytokine receptors and signal transduction", *The FASEB Journal*, 6(15), 1992, pp. 3387–3396.

J. Liu, et al., "Interleukin–6 Signal Transducer gp 130 Mediate Oncostatin M Signaling", *The Journal of Biological Chemistry*, 267(24), 1992, pp. 16763–16766.

M. Abramson et al., "Collagenase Activity in Epidermoid Carcinoma of the Oral Cavity and Larynx", *Annals of Otology*, 84, 1975, pp. 158–163.

B. R. Avalos et al., "K562 Cells Produce and Respond to Human Erythroid–Potentiating Activity", *Blood*, 71, 1988, pp. 1720–1725.

M. J. Banda and Z. Werb, "Mouse Macrophage Elastase", *Biochemical Journal*, 193, 1981, pp. 589–605.

P. Basset et al., "A Novel Metalloproteinase Gene Specifically Expressed in Stromal Cells of Breast Carcinomas", *Nature*, 348, 1990, pp. 699–704.

E. A. Bauer et al., "Enhanced Collagenase Production by Fibroblasts Derived from Human Basal Cell Carcinomas", *Cancer Research*, 39, 1979, pp. 4594–4599.

M. B. Berman, "Collagenase and Corneal Ulceration", in *Collagenase in Normal and Pathological Connective Tissues*, D. E. Wooley and J. M. Evanson, eds., John Wiley & Sons Ltd., New York, NY, 1980, pp. 141–174.

C. Biswas and J. Gross. "Fibroblast–Tumor Cell Interactions and Collagenase Production", *Journal of Cell Biology*, 91, 1981, p. 163a.

T. C. Boone et al., "cDNA Cloning and Expression of a Metalloproteinase Inhibitor Related to Tissue Inhibitor of Metalloproteinases", *Proceedings of the National Academy of Sciences, USA*, 87, 1990, pp. 2800–2804.

T. J. Brown et al., "Purification and Characterization of Cytostatic Lymphokines Produced by Activated Human T Lymphocytes", *Journal of Immunology*, 139, 1987, pp. 2977–2983.

T. E. Cawston and A. J. Barrett, "A Rapid and Reproducible Assay for Collagenase Using [1–$^{14}$C] Acetylated Collagen", *Analytical Biochemistry*, 99, 1979, pp. 340–345.

T. E. Cawston et al., "Identification of a New Metalloproteinase Inhibitor that Forms Tight–Binding Complexes with Collagenase", *Biochemical Journal*, 269, 1990, pp. 183–187.

Y.–H. Chang et al., "Adjuvant Polyarthritis: IV. Induction by a Synthetic Adjuvant: Immunologic, Histopathologic, and Other Studies", *Arthritis and Rheumatism*, 23, 1980, pp. 62–71.

S. D. Clark et al., "Regulation of the Expression of Tissue Inhibitor of Metalloproteinases and Collagenase by Retinoids and Glucocorticoids in Human Fibroblasts", *Journal of Clinical Investigation*, 80, 1987, pp. 1280–1288.

P. Cnomcyznski and N. Sacchi, "Single–Step Method of RNA Isolation by Acid Guanidinium Thiocyanate–Phenol–Chloroform Extraction", *Analytical Biochemistry*, 162, 1987, pp. 156–159.

C. S. Craik, "Use of Oligonucleotides for Site–Specific Mutagenesis", *Biotechniques*, Jan./Feb. 1985, pp. 12–19.

D. D. Dean et al., "Evidence for Metalloproteinase and Metalloproteinase Inhibitor Imbalance in Human Osteoarthritic Cartilage", *Journal of Clinical Investigation*, 84, 1989, pp. 678–685.

(List continued on next page.)

*Primary Examiner*—Vasu S. Jagannathan
*Assistant Examiner*—K. Cochrane Carlson
*Attorney, Agent, or Firm*—Kenyon & Kenyon

[57] ABSTRACT

A method for decreasing metalloproteinase activity in a patient that comprises the step of administering to said patient a therapeutic composition comprising the cytokine oncostatin-M, or a biologically active fragment, mutant, analog or fusion construct thereof. Also, a method for increasing TIMP activity in a patient that comprises the step of administering to said patient a therapeutic composition comprising the cytokine oncostatin-M, or a biologically active fragment, mutant, analog or fusion construct thereof. In addition a method for inhibiting or treating progression of a tumor in a patient that comprises the step of administering to said patient a therapeutic composition comprising oncostatin-M, or a biologically active fragment, mutant, analog, or fusion construct thereof, said method being effective to inhibit invasion by a tumor cell through an extracellular space, extracellular matrix, basement membrane, interstitial tissue or connective tissue. Also methods effective to treat inflammatory or degenerative disease, methods effective to stimulate erythropoiesis, and methods effective to regulate tissue remodeling and to promote healing of injury.

5 Claims, 4 Drawing Sheets

OTHER PUBLICATIONS

D. D. Dean et al., "Levels of Metalloproteases and Tissue Inhibitor of Metalloproteases in Human Osteoarthritic Cartilage", *Journal of Rheumatology*, 14(Suppl. 14), 1987, pp. 43–44.

Y. A. DeClerck et al., "Purification and Characterization of Two Related but Distinct Metalloproteinase Inhibitors Secreted by Bovine Aortic Endothelial Cells", *Journal of Biological Chemistry*, 264(29), 1989, pp. 17445–17453.

A. J. P. Docherty and G. Murphy, "The Tissue Metalloproteinase Family and the Inhibitor TIMP: A Study Using cDNAs and Recombinant Proteins", *Annals of the Rheumatic Diseases*, 49, 1990, pp. 469–479.

A. J. P. Docherty et al., "Sequence of Human Tissue Inhibitor of Metalloproteinases and Its Identity to Erythroid–Potentiating Activity", *Nature*, 318, 1985, pp. 66–69.

D. R. Edwards et al., "Transforming Growth Factor Beta Modulates the Expression of Collagenase and Metalloproteinase Inhibitor", *The EMBO Journal*, 6(7), 1987, pp. 1899–1904.

G. H. Fey and G. M. Fuller, "Regulation of Acute Phase Gene Expression by Inflammatory Mediators", *Mole. Biol. Med.*, 4, 1987, pp. 323–338.

G. H. Fey and J. Gauldie, "The Acute Phase Response of the Liver in Inflammation", *Progress in Liver Diseases*, 9, (Chapter 7), 1990, pp. 89–116.

G. S. Firestein et al., "Gene Expression (Collagenase, Tissue Inhibitor of Metalloproteinases, Complement, and HLA–DR) in Rheumatoid Arthritis and Osteoarthritis Synovium", *Arthritis and Rheumatism*, 34, 1991, pp. 1094–1105.

S. M. Frisch and H. E. Ruley, "Transcription from the Stromelysin Promoter is Induced by Interleukin–1 and Repressed by Dexamethasone", *The Journal of Biological Chemistry*, 262, 1987, pp. 16300–16304.

S. Garbisa et al., "Secretion of Type IV Collagenolytic Protease and Metastatic Phenotype: Induction by Transfection with c–Ha–ras but not c–Ha–ras plus Ad2–E1a", *Cancer Research*, 47, 1987, pp. 1523–1528.

J. C. Gasson, "Molecular Characterization and Expression of the Gene Encoding Human Erythroid–Potentiating Activity", *Nature*, 315, 1985, pp. 768–771.

D. J. Giard et al., "In Vitro Cultivation of Human Tumors: Establishment of Cell Lines Derived from a Series of Solid Tumors", *Journal of National Cancer Institute*, 51, 1973, pp. 1417–1423.

H. C. Grillo and J. Gross, "Collagenolytic Activity During Mammalian Wound Repair", *Developmental Biology*, 15, 1967, pp. 300–317.

A. N. Halaka et al., "Production of Collagenase and Inhibitor (TIMP) by Intracranial Tumors and Dura in Vitro", *Journal of Neurosurgery*, 59, 1983, pp. 461–466.

E. D. Harris, Jr. et al., "Mechanism of Destruction of Articular Structures in Rheumatoid Arthritis", in *Immunopathology of Inflammation*, B. K. Forscher and J. C. Houck, eds., Excerpta Medica, Amsterdam, 1971, pp. 243–253.

K. Hashimoto et al., "Collagenlytic Activities of Squamous Cell Carcinoma of the Skin", *Cancer Research*, 33, 1973, pp. 2790–2801.

T. Hayakawa et al., "Growth–Promoting Activity of Tissue Inhibitor of Metalloproteinases–1 (TIMP–1) for a Wide Range of Cells", *FEBS Letters*, 298(1), 1992, pp. 29–32.

T. Hayakawa et al., "Tissue Inhibitor of Metalloproteinases from Human Bone Marrow Stromal Cell Line KM 102 Has Erythroid–Potentiating Activity Suggesting its Possibly Bifunctional Role in the Hematopoietic Microenvironment", *FEBS Letters*, 268(1), 1990, pp. 125–128.

I. Hellström et al., "Monoclonal Mouse Antibodies Raised Against Human Lung Carcinoma", *Cancer Research*, 46, 1986, pp. 3917–3923.

G. S. Herron et al., "Secretion of Metalloproteinases by Stimulated Capillary Endothelial Cells", *The Journal of Biological Chemistry*, 261, 1986, pp. 2810–2813.

N. J. Hicks et al., "A Fibrosarcoma Model Derived from Mouse Embryo Cells: Growth Properties and Secretion of Collagenase and Metalloproteinase Inhibitor (TIMP) by Tumour Cell Lines", *International Journal of Cancer*, 33, 1984, pp. 835–844.

D. Horn et al., "Regulation of Cell Growth by Recombinant Oncostatin M", *Growth Factors*, 2, 1990, pp. 157–165.

M. Jordana et al., "Heterogeneous Proliferative Characteristics of Human Adult Lung Fibroblast Lines and Clonally Derived Fibroblasts from Control and Fibrotic Tissue", *American Review of Respiratory Diseases*, 137, 1988, pp. 579–584.

J. C. Kallestad et al., "Disulfide Bond Assignment and Identification of Regions Required for Functional Activity of Oncostatin M", *Journal of Biological Chemistry*, 266, 1991, pp. 8940–8945.

L. D. Kerr et al., "Transforming Growth Factor $\beta 1$ and cAMP Inhibit Transcription of Epidermal Growth Factor–and Oncogene–induced Transin RNA", *Journal of Biological Chemistry*, 263(32), 1988, pp. 16999–17005.

R. Khokha and D. T. Denhardt, "Matrix Metalloproteinases and Tissue Inhibitor of Metalloproteinases: A Review of Their Role in Tumorigenesis and Tissue Invasion", *Invasion and Metastasis*, 9, 1989, pp. 391–405.

R. Khokha et al., "Antisense RNA–Induced Reduction in Murine TIMP Levels Confers Oncogenicity on Swiss 3T3 Cells", *Science*, 243, 1989, pp. 947–950.

B. B. Knowles et al., "Human Hepatocellular Carcinoma Cell Lines Secrete the Major Plasma Proteins and Hepatitis B Surface Antigen", *Science*, 209, 1980, pp. 497–499.

W. Kramer et al., "The Gapped Duplex DNA Approach to Oligonucleotide–Directed Mutation Construction", *Nucleic Acids Research*, 12, 1984, pp. 9441–9456.

T. A. Kunkel, "Rapid and Efficient Site–Specific Mutagenesis Without Phenotypic Selection", *Proceedings of the National Academy of Science, USA*, 82, 1985, pp. 488–492.

P. S. Linsley et al., "Identification and Characteriazation of Cellular Receptors for the Growth Regulator, Oncostatin M", *Journal of Biological Chemistry*, 264(8), 1989, pp. 4282–4289.

P. S. Linsley et al., "Cleavage of a Hydrophilic C–Terminal Domain Increases Growth–Inhibitory Activity of Oncostatin M", *Molecular and Cellular Biology*, 10(5), 1990, pp. 1882–1890.

L. A. Liotta et al., "Role of Collagenases in Tumor Cell Invasion", *Cancer and Metastasis Reviews*, 1, 1982, pp. 277–288.

L. A. Liotta et al., "Metasatatic Potential Correlates with Enzymatic Degradation of Basement Membrane Collagen", *Nature*, 284, 1980, pp. 67–68.

M. Lotz and P.–A. Guerne, "Interleukin–6 Induces the Synthesis of Tissue Inhibitor of Metalloproteinases–1/Erythroid Potentiating Activity (TIMP–1/EPA)", *Journal of Biological Chemistry*, 266, pp. 2017–2020.

N. Malik et al., "Molecular Cloning, Sequence Analysis, and Functional Expression of a Novel Growth Regulator, Oncostatin M", *Molecular and Cellular Biology*, 9(7), 1989, pp. 2847–2853.

J. Martel–Pelletier et al., "Neutral Proteases Capable of Proteoglycan Digesting Activity in Osteoarthritic and Normal Human Articular Cartilage", *Arthritis and Rheumatism*, 27(3), 1984, pp. 305–312.

L. M. Matrisian et al., "Isolation of the Oncogene and Epidermal Growth Factor–Induced Transin Gene: Complex Control in Rat Fibroblasts", *Molecular and Cellular Biology*, 6(5), 1986, pp. 1679–1686.

L. M. Matrisian et al., "The mRNA Coding for the Secreted Protease Transin is Expressed More Abundantly in Malignant Than in Benign Tumors", *Proceedings of the National Academy of Sciences, USA*, 83, 1986, pp. 9413–9417.

A. Matsumoto et al., "Stimulation of Bone Collagenase Synthesis by Mouse Fibrosarcoma in Resorbing Bone in vitro Culture", *Archives of Oral Biology*, 24, 1979, pp. 403–405.

C. McDevitt et al., "An Experimental Model of Osteoarthritis: Early Morphological and Biochemical Changes", *Journal of Bone and Joint Surgery*, 59B, 1977, pp. 24–35.

J.–F. Moreau et al., "Leukaemia Inhibitory Factor is Identical to the Myeloid Growth Factor Human Interleukin for DA Cells", *Nature*, 336, 1988, pp. 690–692.

D. E. Mullins and S. T. Rohrlich, "The Role of Proteinases in Cellular Invasiveness", *Biochimica et Biophysica Acta*, 695, 1983, pp. 177–214.

G. Murphy et al., "Metalloproteinases from Rabbit Bone Culture Medium Degrade Types IV and V Collagens, Laminin and Fibronectin", *Biochemical Journal*, 199, 1981, pp. 807–811.

G. Murphy and A. Sellers, "The Extracellular Regulation of Collagenase Activity", in *Collagenase in Normal and Pathological Connective Tissues*, D. E. Wooley and J. M. Evanson, eds., John Wiley & Sons Ltd., London, 1980, Chapter 4, pp. 65–81.

C. M. Overall et al., "Independent Regulation of Collagenase, 72–kDa Progelatinase, and Metalloendoproteinase Inhibitor Expression in Human Fobroblasts by Transforming Growth Factor–β", *Journal of Biological Chemistry*, 264(3), 1989, pp. 1860–1869.

C. M. Overall and J. Sodek, "Initial Characterization of a Neutral Metalloproteinase, Active on Native 3/4–Collagen Fragments, Synthesized by ROS 17/2.8 Osteoblastic Cells, Periodontal Fibroblasts, and Identified in Gingival Crevicular Fluid", *Journal of Dental Research*, 26(7), 1987, pp. 1271–1282.

J.–P. Pelletier et al., "Collagenolytic Activity and Collagen Matrix Breakdown of the Articular Cartilage in Pond–Nuki Dog Model of Osterarthritis", *Arthritis and Rheumatism*, 26(7), 1983, pp. 866–874.

R. R. Pfister and N. Burstein, "The Alkali Burned Cornea: I. Epithelial and Stromal Repair", *Experimental Eye Research*, 23, 1976, pp. 519–535.

M. J. Pond and G. Nuki, "Experimentally–Induced Osteoarthritis in the Dog", *Annals of the Rheumatic Diseases*, 32, 1973, pp. 387–388.

J. J. Reynolds, "The Molecular and Cellular Interactions Involved in Connective Tissue Destruction", *British Journal of Dermatology*, 112, 1985, pp. 715–723.

C. D. Richards et al., "Cytokine Control of Acute Phase Protein Expression", *European Cytokine Network*, 2(2), 1991, pp. 89–98.

C. D. Richards et al., "Recombinant Oncostatin M Stimulates the Production of Acute Phase Proteins in HepG2 Cells and Rat Primary Hepatocytes in Vitro", *The Journal of Immunology*, 148, 1992, pp. 1731–1736.

R. M. Schultz et al., "Inhibition by Human Recombinant Tissue Inhibitor of Metalloproteinases of Human Amnion Invasion and Lung Colonization by Murine B16–F10 Melanoma Cells", *Cancer Research*, 48, 1988, pp. 5539–5545.

H. H. Slansky and C. H. Dohlman, "Collagenase and the Cornea", *Survey of Opthamology*, 14, 1970, pp. 402–416.

J. M. Staurt et al., "Type II Collagen–Induced Arthritis in Rats: Passive Transfer with Serum and Evidence that IgG Anticollagen Antibodies Can Cause Arthritis", *Journal of experimental Medicine*, 155, 1982, pp. 1–16.

W. G. Stetler–Stevenson et al., "Tissue Inhibitor of Metalloproteinase (TIMP–2)", *Journal of Biological Chemistry*, 264(29), 1979, pp. 17374–17378.

U. P. Thorgeirsson et al., "Effect of Natural Protease Inhibitors and a Chemoattractant on Tumor Cell Invasion in Vitro", *Journal of National Cancer Institute*, 69, 1982, pp. 1049–1054.

Z. Werb and S. Gordon, "Elastase Secretion by Stimulated Macrophages", *Journal of Experimental Medicine*, 142, 1975, pp. 361–377.

C. A. Westbrook et al., "Purification and Characterization of Human T–Lymphocyte–Derived Erythroid–Potentiating Activity", *Journal of Biological Chemistry*, 259, 1984, pp. 9992–9996.

B. A. White and F. C. Bancroft, "Cytoplasmic Dot Hybridization: Simple Analysis of Relative mRNA Levels in Multiple Small Cell or Tissue Samples"*Journal of Biological Chemistry*, 257, 1982, pp. 8569–8572.

R. L. Wilder et al., "Strain and Sex Variation in the Susceptibilty to Streptococcal Cell Wall–Induced Polyarthritis in the Rat", *Arthritis and Rheumatism*, 25, 1982, pp. 1064–1072.

G. Wirl and J. Frick, "Collagenase–A Marker Enzyme Human Bladder Cancer?", *Urological Research*, 7, 1979, pp. 103–108.

J. F. Woessner Jr., "A Latent Form of Collagnase in the Involuting Rat Uterus and its Activation by a Serine Proteinase", *Biochemical Journal*, 161, 1977, pp. 535–542.

J. F. Woessner Jr., "Matrix Metalloproteinase and their Inhibitors in Connective Tissue Remodeling", *FASEB Journal*, 5, 1991, pp. 2145–2154.

D. E. Woolley et al., "Collagenase at Sites of Cartilage Erosion in the Rheumatoid Joint", *Arthritis and Rheumatism*, 20, 1977, pp. 1231–1239.

D. E. Woolley et al., "Collagenase Immunolocalization Studies of Rheumatoid and Malignant Tissues", in *Collagenase in Normal and Pathological Connective Tissues*, D. E. Wooley and J. M. Evanson, eds., John Wiley & Sons Ltd., New York, NY, 1980, Chapter 6, pp. 105–125.

J. K. Wright et al., "Transforming Growth Factor Beta Stimulates the Production of the Tissue Inhibitor of Metalloproteinases (TIMP) by Human Synovial and Skin Fibroblasts", *Biochemica et Biophysica Acta*, 1094, 1991, pp. 201–210.

Y. Yamanishi et al., "Collagenolytic Activity in Malignant Melanoma: Physicochemical Studies", *Cancer Research*, 33, 1973, pp. 2507–2512.

Y. Yamanishi et al., "Effect of Collagenolytic Activity in Basal Cell Epithelioma of the Skin on Reconstituted Collagen and Physical Properties and Kinetics of the Crude Enzyme", *Cancer Research*, 32, 1972, pp. 2551–2560.

J. M. Zarling et al., "Oncostatin M: A Growth Regulator Produced by Differentiated Histiocytic Lymphoma Cells", *Proceedings of the National Academy of Sciences, USA*, 83, 1986, pp. 9739–9743.

B. C. Nair et al., "Identification of a Major Growth Factor for AIDS–Kaposi's Sarcoma Cells as Oncostatin M", *Science*, 255, 1992, pp. 1430–1432.

S. A. Miles et al., "Oncostatin M as a Potent Mitogen for AIDS–Kapos's Sarcoma–Derived Cells", *Science*, 255, 1992, pp. 1432–1434.

D. P. Gearing et al., "The IL–6 Signal Transducer, gp130: An Oncostatin M Receptor and Affinity Converter for the LIF Receptor", *Science*, 255, 1992, 1434–1437.

H. Baumann and J. Gauldie, "Regulation of Hepatic Acute Phase Plasma Protein Genes by Hepatocyte Stimulating Factors and Other Mediators of Inflammation", *Mole. Biol. Med.*, 7, 1990, pp. 147–159.

T. J. Brown et al., "Regulation of IL–6 Expression by Oncostatin M", *The Journal of Immunology*, 147(7), 1991, pp. 2175–2180.

P. S. Linsley and J. C. Kallestad, "Novel Proteins with Oncostatin M Activity and Process for Their Preparation", International Application Number PCT/US90/07227, published on Jun. 27, 1991, bearing Publication Number WO91/09057.

Buno et al 1989 Exp Hematol 17:1038.

Rose et al 1991 PNAS 88:8641.

REGULATION OF CELLULAR INVASIVENESS

FIELD OF THE INVENTION

This invention relates to regulation of cellular invasiveness, a process by which one or more cells invade a tissue, and in so doing, penetrate a barrier of extracellular matrix. Cellular invasiveness is important in the progression of many pathological conditions including malignant cancer and inflammatory or degenerative disease such as arthritis. Cellular invasiveness is also an important aspect of certain normal physiological processes such as regeneration of injured tissue. This invention pertains therefore to treatment of disease involving cellular invasiveness or degradation of extracellular matrix. This invention pertains also to enhancement of desired physiological processes that involve tissue reorganization or regeneration.

Cellular invasiveness is an important aspect of many pathological and also many normal physiological events. It may be defined broadly as the capability of a cell to penetrate and colonize a tissue, typically, but not always, a histologically dissimilar one. "Tissue" is broadly defined as an aggregation of cells usually of one or only a few types organized for a particular function.

Typically, invasion requires that the invading cell cross a barrier substance that delineates a boundary between tissues or that forms an extracellular scaffolding (between member cells) that stabilizes the structure of the tissue. Representative of such barrier substances are extracellular matrix, basement membrane, interstitial tissue and connective tissue. For the purposes of the invention, and as elaborated below, all such substances are referred to hereinafter as "extracellular matrix."

The cells of tissues are generally in contact with a network of large extracellular macromolecules that occupies the spaces in a tissue between the component cells and also occupies the space between adjacent tissues. This extracellular matrix functions as a scaffolding on which the cells and tissue are supported and is involved actively in regulating interaction of the cells that contact it. The principal macromolecules of the extracellular matrix include the collagens (the most abundant proteins in the body) and glycosaminoglycans (complex polysaccharides which are usually bonded also to protein and then termed proteoglycans). The macromolecules that comprise the extracellular matrix are produced typically by the cells in contact therewith, for example, epithelial cells in contact with a basement membrane and fibroblasts embedded in connective tissue.

The glycosaminoglycan (proteoglycan) molecules form a highly hydrated matrix (a gel) in which elastic or fibrous proteins (such as collagen fibers) are embedded. The aqueous nature of the gel permits diffusion of metabolically needed substances between the cells of a tissue and between tissues. Additional proteins that may be found in extracellular matrix include elastin, fibronectin and laminin.

The term "connective tissue" refers to extracellular matrix plus specialized cells such as, for example, fibroblasts, chondrocytes, osteoblasts, macrophages and mast cells found therein. The amount of connective tissue in organs varies considerably. The brain or spinal cord contain very little whereas skin is composed (on a weight basis) mostly of extracellular matrix components. The term "interstitial tissue" is best reserved for an extracellular matrix that stabilizes a tissue internally, filling the gaps between the cells thereof. There are also specialized forms of extracellular matrix (connective tissue) that have additional functional roles—cornea, cartilage and tendon, and when calcified, the bones and teeth.

A structural form of extracellular matrix of particular importance to the practice of the invention is the basal lamina (basement membrane). Basal laminae are thin zones of extracellular matrix that are found under epithelium or surrounding, for example, muscle cells or the cells that electrically insulate nerve fibers. Generally speaking, basal laminae separate cell layers from underlying zones of connective tissue or serve as a boundary between two cell layers. Of particular relevance to the practice of the invention is that a basal lamina can serve as a pathway for invading cells associated with pathologic processes, or for structural organization associated with tissue repair (i.e. as a blueprint from which to regenerate original tissue architecture and morphology).

Accordingly, this invention relates to regulation of extracellular matrix metabolism in both physiologically desirable contexts (such as tissue repair) and also as associated with pathological conditions as described further below.

REPORTED DEVELOPMENTS

It is well established that cellular invasiveness involves secretion by invading cells of particular proteinases. These proteinases comprise enzymes that break down particular protein-containing components of the above mentioned types of barrier materials, for example, collagens, elastins and proteoglycans. A general review of the involvement of proteinases in cellular invasion is provided by Mullins, D. E. and Rohrlich, S. T. Biochemica et Biophysica Acta, 695, 177–214 (1983).

The capacity for cellular invasiveness (and proteinase production) by an invading cell is of particular importance to the distinction between a malignant cancer and a benign tumor. A benign tumor exists without concomitant degradation of the basement membrane that separates the host tissue (the tissue of tumor origin) from surrounding tissues. Such localized tumors are often removed readily by surgery.

In contrast, metastasis defines a process whereby tumor cells escape from the primary tumor mass and colonize new sites, typically protected by extracellular matrix. Successful metastasis involves compromise of extracellular matrix covering or within an affected tissue. Typically, unless all tumor cells possessing this capability are killed, growth or regrowth of tumor masses at distant locations is likely, followed ultimately by serious structural and functional disruption of affected organs. Schultz, R. M. et al Cancer Research, 48, 5539–5545 (1988), describe a representative metastatic process as involving "(a) detachment of the metastatic tumor cell from the primary tumor, (b) invasion through the extracellular protein matrix and basement membrane surrounding the capillaries with intravasation into the capillary bed followed by migration in the bloodstream, (c) attachment of the tumor cells to the vascular wall in the capillaries of the target tissue, (d) extravasation from the capillaries through the basement membrane and extracellular matrix protein surrounding the capillary, and then (e) growth into the target organ to form a new tumor."

As mentioned, of central importance to the metastatic process and other processes involving cellular invasiveness is the activity of proteinases. A very important fraction of total proteinase activity associated with cellular invasiveness is that contributed by metalloproteinases. Metalloproteinases are defined generally as a group of proteolytic enzymes that generally contain tightly associated zinc ions, usually require calcium ions for maximal activity, typically cleave internal instead of external peptide bonds in the substrate protein, and usually have maximal activity at around neutral pH. See, for example, Khokha, R. and Denhardt, D. T. *Invasion Metastasis*, 9, 391–405 (1989). As elaborated below, certain of these proteinases contain also amino acid and structural homologies. Docherty, A. J. P. and Murphy, G. *Annals of the Rheumatic Diseases*, 49, 469–479 (1990).

Evidence for the important contribution of metalloproteinases to both normal and pathological processes involving cellular invasion is extensive. For a review thereof see, for example, Mullins, D. E. and Rohrlich, S. T., cited above. A strong correlation between production of metalloproteinase by a transformed (tumor) cell and the metastatic potential of such a cell has been demonstrated. See Liotta, L. A. et al. *Cancer Metastasis Rev.*, 1, 277–288 (1982), Liotta, L. A. et al. *Nature (Lond.)*, 284, 67–68 (1980), and Garbisa, S. et al. *Cancer Res.*, 47, 1523–1528 (1987). See also Halaka, A. N. et al. *J. Neurosurgery*, 59, 461–466 (1983), and references cited therein. In addition, many types of tumor cells are believed to stimulate adjacent normal cells (such as connective tissue fibroblasts at the site of invasion) to produce additional metalloproteinase. Bauer, E. A. et al. *Cancer Res.*, 39, 4594–4599 (1979), Matsumoto, A. et al. *Arch. Oral Biol.*, 24, 403–405 (1979), and Wirl, G. and Frick, J. *Urol. Res.*, 7, 103–108 (1979).

Elevated levels of metalloproteinase activity are also associated with tissue degradation found in arthritic disease. See, for example, Martel-Pelletier, J. et al. *Arthritis and Rheumatism*, 27 (3), 305–312 (1984), and Dean, D. D. et al. *J. Rheumatol*, 14 (suppl 14), 43–44 (1987). Metalloproteinase activity is also implicated in the pathology of many kinds of inflammation and in improper angiogenesis (capillary development) associated with diabetic retinopathy.

Wound healing and normal tissue remodeling are also believed to be affected by the level of metalloproteinase activity available at the relevant site and the regulation thereof. Woessner, J. F. *Biochemical Journal*, 161, 535–542 (1977); Woessner, J. F. *FASEB Journal*, 5, 2145–2154 (1991); Herron, et al. *J. Biol. Chem.*, 261, 2810–2813 (1986). Healing of wounds, for example, involves substantial remodeling of tissue. Although such a process is not invasive per se, it involves localized breakdown of extracellular matrix and the breaking and forming of cell attachments. It is apparent that regulation of metalloproteinase activity in both normal and pathological processes is of great importance in a variety of clinical contexts.

The level of metalloproteinase activity in extracellular matrix of the body is regulated by a number of control mechanisms. Typically metalloproteinases are secreted in inactive ("pro" proteinase) form and must be activated (usually with a change in conformation) by other proteinases. Additionally certain steroid hormones, for example β-estradiol (the major estrogen) and progesterone inhibit metalloproteinase expression. Expression of metalloproteinase has also been inhibited by glucocorticoid steroids. Pathologic conditions such as arthritic degeneration and metastasis of tumor cells reflect upset of normal regulation. A variety of experimental results described in the literature suggest potentially useful methods to regulate metalloproteinase activity at a site in a patient affected with disease, or at which, for example, wound healing or tissue remodeling is taking place.

Exposure of transformed MRC-5 human fetal lung fibroblasts to transforming growth factor β (hereinafter "TGF-β") resulted in decreased metalloproteinase expression. Edwards, D. R. et al. *EMBO Journal*, 6 (7), 1899–1904 (1987). See also Kerr, L. D. et al. *J. Biol. Chem.*, 263 (32), 16999–17005 (1988) concerning decreased expression of a metalloproteinase (transin) caused by TGF-β in transformed rat cells. TGF-β is known to exist in many forms the use of which being within the practice of the present invention if the appropriate functional activity is present.

An additional therapy is glucocorticoid treatment which has been demonstrated in vitro to downregulate type-1 (pro)collagenase and (pro)stromelysin expression. Firsch and Ruley, *J. Biol. Chem.*, 262, 16300–16304 (1987). For in vivo data on metalloproteinase downregulation see Firestein, G. et al. *Arthritis & Rheumatism*, 34, 1094–1105 (1991).

However, an alternative form of metalloproteinase regulation for use in patients is based on a particular and effective pathway of metalloproteinase regulation that operates in vertebrate tissues, that is, the interaction of metalloproteinase with the protein "TIMP" (tissue inhibitor of metalloproteinase). TIMP protein is known to form a complex (often an irreversible 1:1 complex) with metalloproteinase. As described below, multiple forms of "TIMP" are known to exist. That which is best characterized is a glycoprotein called TIMP-1 having a peptide backbone weight of about 21 kDa (kilodaltons) and a final (glycosylated) weight in vivo of about 28 kDa. TIMP-1 is produced and secreted by the cells of all connective tissues, Murphy, G. and Sellers, A. The Extracellular Regulation of Collagenase Activity, in *Collagenase in Normal and Pathological Connective Tissues*, Woolley, D. E. and Evanson, J. M. eds., 65–81, John Wiley, London (1980), and by, for example, aortic endothelial cells, DeClerck, Y. et al. *J. Biol. Chem.*, 264 (29), 17445–17453 (1989). TIMP-1 can be detected also in many body fluids, and is produced by cells of most types of mammalian tissue. The DNA and amino acid sequences for certain forms of TIMP protein have been deduced, and the expression of certain TIMP proteins from recombinant host cells has been accomplished. Docherty, A. J. P. et al. *Nature*, 318, 66–69 (1985), Boone, T. C. et al. *Proc. Natl. Acad. Sci. USA*, 87, 2800–2804 (1990); Docherty, A. J. P. and Murphy, G. *Annals of Rheumatic Disease*, 49, 469–479 (1990).

There is substantial evidence that control of cellular invasiveness and of degradation of extracellular matrix may be accomplished by regulating the concentration of TIMP available at the target site. (See also discussion below of the recently discovered metalloproteinase inhibitor "LIMP") An inverse correlation has been established between the invasive potential of intracranial tumor cells and the levels of TIMP production thereby. Halaka, A. et al. *J. Neurosurgery*, 59, 461–466 (1983). See also Hicks, N. J. et al. *Int. J. Cancer*, 33, 835–844 (1984). TIMP has been demonstrated to inhibit invasion of the human amnion by certain sarcoma cells. Thorgeinsson, U. P. et al. *J. Natl. Cancer Inst.*, 69, 1049–1054 (1982). Intraperitoneal infusions of TIMP have been demonstrated to inhibit colonization of mouse lung by certain subcutaneously injected melanoma cells. Schultz, R. M. *Cancer Res.*, 48, 5539–5545 (1988). Khokha, R. et al. *Science*, 743, 947–950 (1989) have demonstrated that transformed but noninvasive mouse 3T3 cells that were then downregulated for TIMP production (by incorporation of DNA encoding antisense TIMP mRNA) became invasive.

Thus, the development of methods to induce increased levels of TIMP in a patient or to otherwise regulate the production or availability of TIMP at a particular tissue site is of great clinical importance.

A number of observations reported in the literature suggest approaches that might be effective to increase TIMP activity in patients. Clark, S. D. et al. *J. Clin. Invest*, 80, 1280–1288 (1987) demonstrated that certain retinoid compounds (vitamin A derivatives) increased production of TIMP in a dose dependent fashion in monolayer cultures of human fibroblasts. A decrease in collagenase (a metalloproteinase) mRNA was also detected.

Similarly, Lotz, M. and Guerne, P. A. *J. Biol. Chem.*, 266, 2017–2020 (1991) have shown that a multifunctional cytokine protein, interleukin-6 ("IL-6"), enhances production of TIMP by human fibroblasts but does not enhance metalloproteinase activity. However, owing to the multifunctional nature of IL-6 and reports of its toxicity, it is unlikely that IL-6 alone will provide an optimized method for elevating TIMP activity and decreasing metalloproteinase activity in patients.

Razoxane, an anti-cancer and anti-psoriasis compound has been tested for its effects on TIMP activity using monolayer cultures of rabbit chondrocyte cells. Reynolds, J. J., *British Journal of Dermatology*, 112, 715–723 (1985). Chondrocyte collagenase synthesis was inhibited whereas TIMP expression increased. However, razoxane and its derivatives may be insufficiently potent to suggest their use in a promising therapeutic composition.

Transforming growth factor B has been demonstrated to inhibit collagenase (metalloproteinase) induction while increasing the expression of TIMP in cultured quiescent human fibroblasts (Edwards, D. R. et al. *The EMBO Journal*, 6 (7), 1899–1904 (1987)). Additionally, interleukin-1, another cytokine, has been demonstrated to increase expression of TIMP, however with concomitant increased expression of undesired metalloproteinase activity.

Accordingly, provision of an effective method to increase TIMP activity and to decrease metalloproteinase activity in a patient has utility in the clinical treatment of cancer and of inflammatory and degenerative disease. Such methods also have utility in the clinical management of physiological processes that involve tissue reorganization and regeneration.

It has also been determined that human TIMP-1 protein is identical to a human protein known previously as erythroid-potentiating activity ("EPA"), said protein having utility in the clinical treatment of diseases or conditions involving a efficiency of red blood cells.

SUMMARY OF THE INVENTION

This invention relates to the discovery that administration to a patient of a therapeutic composition comprising the cytokine oncostatin-M increases TIMP activity and decreases metalloproteinase activity in tissues thereof. This invention relates also to the discovery that administration to a patient of a therapeutic composition comprising the cytokine oncostatin-M is effective to inhibit the invasive or metastatic potential of tumor cells.

Accordingly, there is provided a method for increasing TIMP activity in a patient that comprises the step of administering to said patient a therapeutic composition comprising the cytokine oncostatin-M, or a biologically active fragment, mutant, analog or fusion construct thereof. There is also provided a method for decreasing metalloproteinase activity in a patient that comprises the step of administering to said patient a therapeutic composition comprising the cytokine oncostatin-M, or a biologically active fragment, mutant, analog or fusion construct thereof.

The methods of the invention are particularly effective in increasing TIMP activity and/or decreasing metalloproteinase activity in extracellular spaces, extracellular matrices, basement membranes, and connective and interstitial tissues (hereinafter collectively referred to as "extracellular matrix") of a patient. The invention will be practiced widely in the medical art to inhibit or treat progression of tumors in patients, and in particular, to inhibit the invasive or metastatic potential of tumor cells.

Speaking more generally, regulation with oncostatin-M of TIMP activity and of metalloproteinase activity are important aspects of clinical therapy for any disease that involves damage to extracellular matrix. In accord with the practice of the invention, regulation of TIMP activity and of metalloproteinase activity using oncostatin-M are also important aspects of therapy for tissue remodeling, and/or to promote the healing of injury.

Representative of inflammatory or degenerative diseases that may be treated with oncostatin-M according to the practice of the invention are rheumatoid arthritis, osteoarthritis, periodontal disease, diabetic retinopathy, emphysema, atherosclerosis, and pneumonia (whether of viral, bacterial or chemical origin).

Another aspect of the invention encompasses a method for increasing the concentration of liver-derived acute phase proteins secreted by a patient in response to inflammation that comprises the step of administering to said patient a therapeutic composition comprising the cytokine oncostatin-M, or a biologically active fragment, mutant, analog, or fusion construct thereof.

Still another aspect of the invention encompasses provision of a method for stimulating erythropoiesis in a patient that comprises the step of administering a therapeutic composition comprising the cytokine oncostatin-M, or a biologically active fragment, mutant, analog or fusion construct thereof.

Use of the processes and the therapeutic compositions of the invention is applicable also in the treatment of mammals other than humans, and as described below, oncostatin-M or a biologically active fragment, mutant, analog or fusion construct thereof derived from other mammals can be used therapeutically in human patients.

DETAILED DESCRIPTION OF THE INVENTION

As set forth above, both cellular invasiveness and breakdown of extracellular matrix are important aspects of many pathological and also many normal physiological processes. Rate and extent of cellular invasiveness and/or of breakdown of extracellular matrix are affected significantly by the level of metalloproteinase activity available at the affected site(s). Therapeutic regulation of metalloproteinase activity (whether to repair or maintain tissue integrity or to inhibit or treat pathological processes) can be accomplished by altering the level of TIMP activity in a patient, or at an affected site therein.

In the practice of this invention, "TIMP activity" refers to an activity or capability to inhibit degradation of macromolecules of the extracellular matrix in a patient, said inhibition being caused, in whole or in part, by one or more species of peptide defined hereinafter as "TIMP." Similarly, "metalloproteinase activity" refers to an activity or capability to degrade one or more species of macromolecule of the extracellular matrix in a patient, said degradation being caused, in whole or in part, by one or more species of protein defined hereinafter as "metalloproteinase."

It has now been discovered that TIMP activity in a patient, or at an affected site therein, can be regulated by administering therapeutic compositions comprising oncostatin-M, or a biologically active fragment, mutant, analog or fusion construct thereof. In the practice of this invention, use of the term "oncostatin-M" is intended to refer also to the above mentioned biologically active variants.

Accordingly, this invention provides a novel and surprisingly effective method for increasing TIMP activity in a patient and effective methods to (a) inhibit the invasive or metastatic potential of tumor cells; (b) treat inflammatory and/or degenerative disease; (c) to enhance physiological processes that involve tissue remodeling and healing of injury; and (d) to stimulate production of red blood cells.

Figure 1:
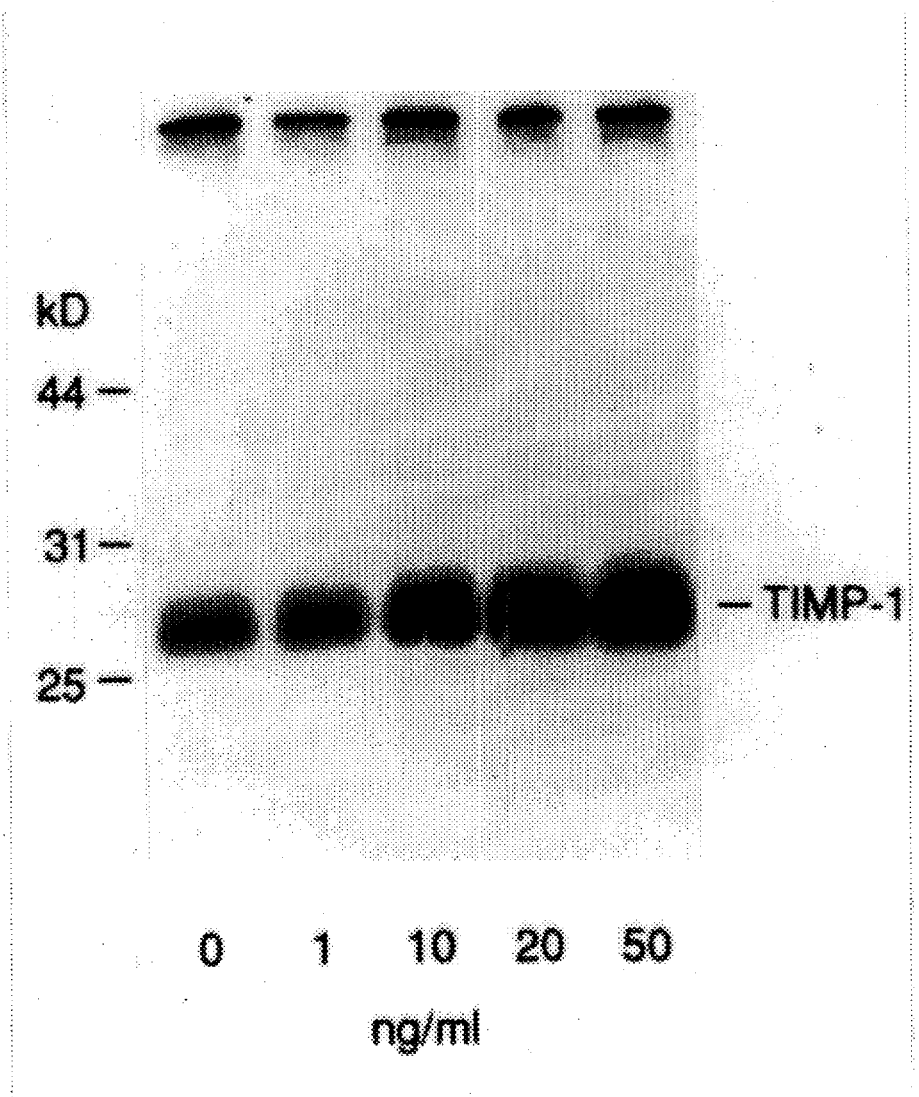
FIG. 1 depicts an autoradiograph of a polyacrylamide gel that shows the enhanced production of TIMP-1 protein caused by oncostatin-M.

Example 1 of the invention (see below) demonstrates that the culturing of cells (non-transformed human fibroblasts) in the presence of oncostatin-M leads to substantially increased secretion of TIMP-1 protein. This enhancing effect of oncostatin-M (using doses of from 1 to 50 ng oncostatin-M/ml of culture medium) on secret ion of TIMP-1 protein is very evident (FIG. 1). Example 3 of the invention demonstrates that oncostatin-M (at a concentration of 50 ng/ml in the culture medium) increased either the level of TIMP-1 mRNA in the cultured cells or increased effectiveness (amount or rate) of translation therefrom (see also FIG. 3). As described below, the concentrations of oncostatin-M used herein are comparable to concentrations that are predicted to be effective in the tissues of patients.

Figure 2A:
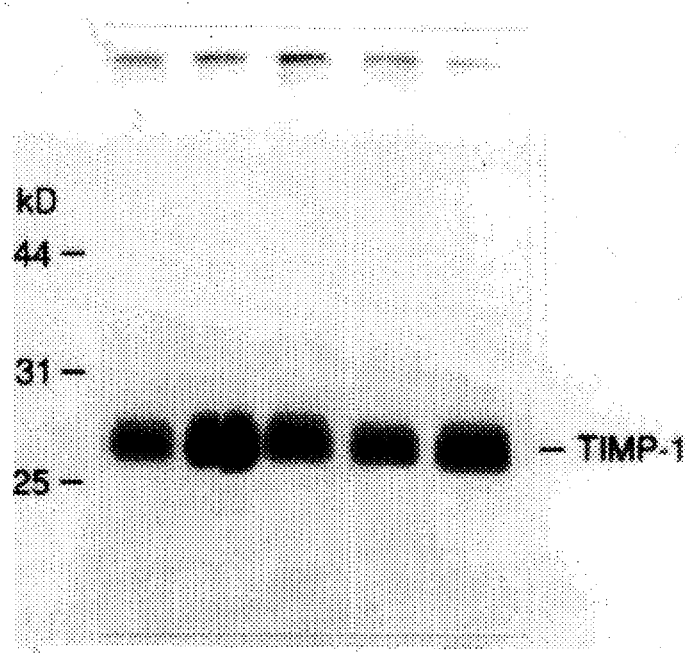
FIG. 2 depicts an autoradiograph of a polyacrylamide gel that shows the effect of certain cytokines on the production of TIMP-1 and type 1 collagenase.
Figure 2B:
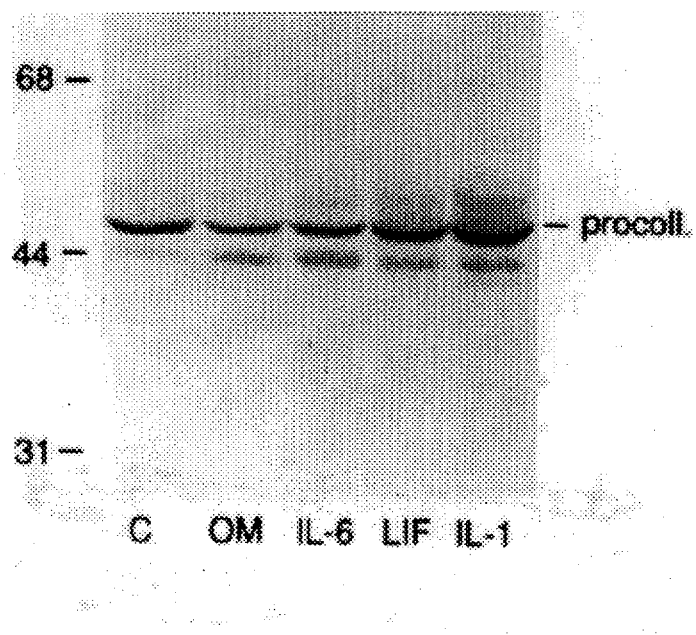
Figure 3A:
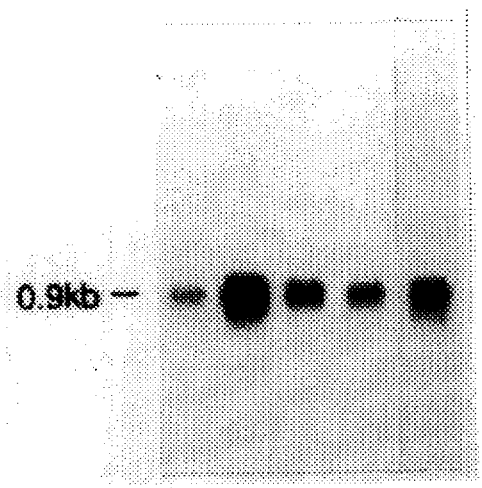
FIG. 3 is a northern blot that demonstrates the effect of certain cytokines on the production by fibroblasts of mRNA encoding TIMP-1 and other proteins.
Figure 3B:
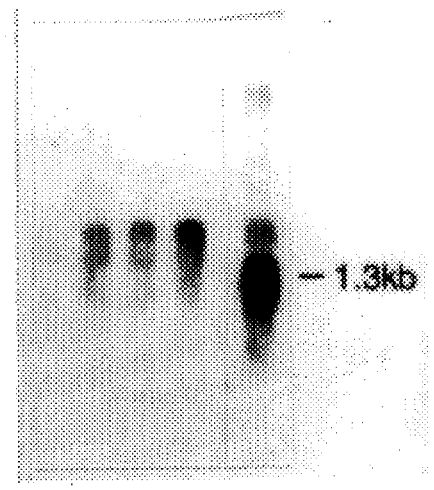
Figure 3C:
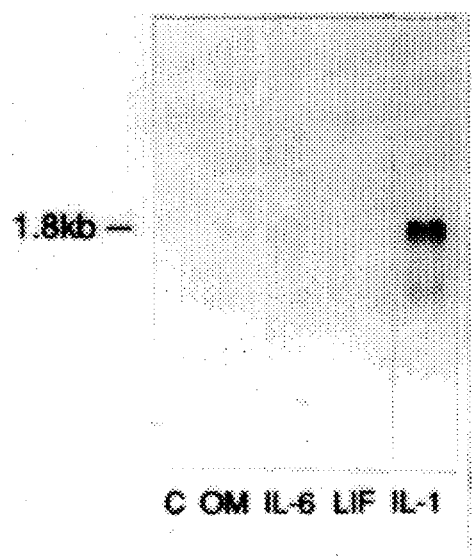
Figure 3D:
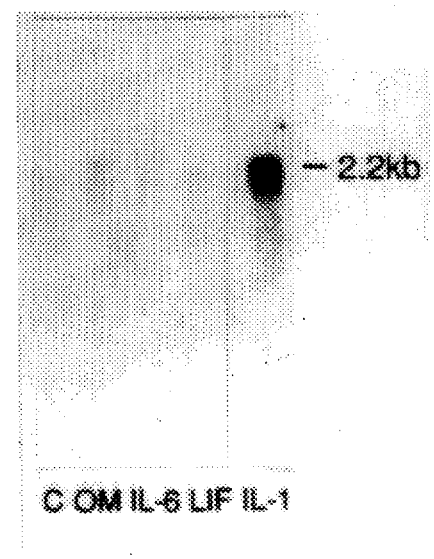

More important than the absolute amount of increase in TIMP activity associated with administration of oncostatin-M, or of oncostatin-M in association with one or more other cytokines, is the increase in TIMP activity relative to the level of resultant metalloproteinase activity. In Example 2 below it is demonstrated that oncostatin-M (at 30 ng/ml) was the most effective of the cytokines tested in increasing TIMP-1 protein expression (FIG. 2, panel A) and that oncostatin-M did not enhance expression of the metalloproteinase collagenase (MMP-1) above control levels (FIG. 2, panel B).

Example 3 demonstrates (using cDNA probes directed to mRNA for type-1 collagenase and stromelysin), that administration of oncostatin-M did not alter steady state levels of MRNA for these metalloproteinases, whereas substantial enhancement of the steady state level of TIMP-1 MRNA resulted.

That the effect of oncostatin-M on TIMP-activity is widely applicable to different types of target cells is demonstrated in Example 4 (see below) by measuring resultant TIMP-1 mRNA levels in H2981 lung carcinoma cells and HepG2 cells. However, no effect was detected for cell line MCF-7 (human breast adenocarcinoma, ATCC HTB 22). This cell line may have defective oncostatin-M receptor complex or a defect in the signal transducing mechanism for oncostatin-M binding. Alternatively, a high basal level of TIMP expression demonstrated under the particular conditions of assay may mask the inducing effect. As expected, no effect of oncostatin-M on TIMP activity was detected for cell line 4.10.1, a human melanoma cell line. This cell line had been previously selected for to lack response to oncostatin-M or interleukin-6. The use thereof served as an assay control.

Information Concerning the Structure of Oncostatin-M and the Design of Therapeutically Active Peptides Derived Therefrom Oncostatin-M is a cytokine polypeptide that regulates growth of cells. It is produced, for example, by macrophages and activated T lymphocytes and has been isolated from supernatants of cultures of histiocytic lymphoma cells type U-937 treated with phorbol ester. Oncostatin-M was determined originally to inhibit growth of a certain human tumor cell line (A375 melanoma cells) and was distinguished also by its inability to inhibit growth of normal human fibroblasts. Oncostatin-M has been determined to inhibit proliferation by a wide variety of tumor cell lines derived from numerous tissues. Horn, D. et al. *Growth Factors*, 2, 157–165 (1990).

Binding sites for oncostatin-M of substantial specificity have been detected on numerous normal and tumor cell types. The presence of different types of binding sites having different affinities for oncostatin-M and the identification of a receptor protein have also been demonstrated. Linsley, P. S. et al. *J. Biol. Chem.* 264(8), 4282–4289 (1989). The series of intracellular events that are responsible for the effects of oncostatin-M on a target cell once it has bound to a receptor, however, are not known.

Methods for the production of oncostatin-M (including methods adaptable to the production of commercial quantities thereof) are provided in European Patent Application No. 88107180.7, published on Nov. 17, 1988 as Publication No. 0 290 948 A2, the text of which is incorporated herein by reference.

A further principal discovery of the invention is the erythropoietic (red blood cell proliferating) activity of oncostatin-M mediated by its ability to increase TIMP activity in a patient.

Oncostatin-M was first described by Zarling, J. M. et al. *Proc. Natl. Acad. Sci. USA*, 83, 9739–9743 (1986) and therein characterized as having an apparent molecular weight of about 18,000 (18 kDa) as determined by gel chromatography and 28 kDa as determined by polyacrylamide gel electrophoresis. See also Brown, et al. *J. Immunol.*, 139, 2977–2983 (1987). The mature (circulating) form of oncostatin-M is a glycoprotein that results from considerable posttranslational processing of a precursor polypeptide, and contains about 196 ($Ala^1$-$Arg^{196}$) amino acid residues. Oncostatin-M is produced originally as a pre-propolypeptide containing a signal peptide of approximately 25 residues that both begins and ends with a methionine residue. An alanine residue forms the amino terminus of the mature human protein in vivo. Malik, N. et al. *Molecular and Cellular Biology*, 9(7), 2847–2853 (1989). After signal peptide cleavage there remains an approximate 227 residue polypeptide ($Ala^1$-$Arg^{227}$) which is further processed by proteolytic cleavage to yield the final $Ala^1$-$Arg^{196}$ (or also $Ala^1$-$Arg^{195}$) circulating polypeptide, Linsley, P. S. et al. *Molecular and Cellular Biology*, 10(5), 1882–1890 (1990). Additionally, further cleavage of residues from the C-terminal domain of oncostatin-M (for example, down to $Ala^1$-$Ser^{185}$) has been demonstrated not to prevent the therapeutic utility of oncostatin-M in the practice of the invention. In this regard, see also International Application No. PCT/US 90/07227, published Jun. 27, 1991 as International Publication No. WO 91/09057, at 5 thereof.

CDNA and genomic cloning for oncostatin-M, the amino acid and DNA sequence analysis therefor, and also expression of functional oncostatin-M polypeptide from recombinant mammalian cells have been reported. Malik, N. et al. *Molecular and Cellular Biology*, 9(7), 2847–2853 (1989).

Considerable information is available concerning the structural organization of the oncostatin-M polypeptide and of the identity of subregions thereof needed for functional activity. Kallestad, J. C. et al. *J. Biol. Chem.*, 264(8), 4282–4289 (1989). The disclosures of the aforementioned Kallestad, J. C. et al. (1989) and Linsley, P. S. et al. (1990) references are incorporated herein specifically by reference.

Therapeutic compositions useful in the practice of the invention comprise oncostatin-M or one or more molecules that are biologically active fragments, mutants, analogs or fusion constructs thereof. For the purposes of the invention all such biologically active molecules are included in the meaning of the term "oncostatin-M" as used herein. Such molecules are considered "biologically active" if they possess two or more of the following properties of oncostatin-M: immunological cross-reactivity with naturally occurring human oncostatin-M, affinity for cellular receptors for oncostatin-M, the capability to increase TIMP activity in a patient, or the capability to decrease metalloproteinase activity in a patient. By "immunological cross reactivity," it is meant that one or more antibodies produced in response to a molecule (typically a peptide) of the invention related to oncostatin-M, will bind specifically to naturally occurring human oncostatin-M polypeptide at a common epitope thereof, or that one or more antibodies produced in response to human oncostatin-M will bind specifically to the analogous molecule where said oncostatin-M and the molecule have a common epitope. By "oncostatin-M receptor" is meant a binding site on the surface of a target cell which binds oncostatin-M with high affinity, said binding being saturable and not inhibited by structurally unrelated peptides. The terms "TIMP activity" and "metalloproteinase activity" are used herein as defined previously.

There are hereafter described representative examples of therapeutic compositions comprising oncostatin-M, and methods for producing and evaluating further such compositions having enhanced pharmaceutical activity.

Aforementioned published European Patent Application No. 88107180.7 describes numerous methods of producing oncostatin-M, for example, from naturally occurring sources (tissues and fluids), and also from recombinant eucaryotic or procaryotic cells. The therapeutic use of all such forms of oncostatin-M is within the practice of the present invention. For example (see the aforementioned European Patent Application at Example 8 thereof), coding sequence for the oncostatin-M gene was expressed from *E. coli*. Methods for the solubilization of aggregated product protein (inclusion body) were described therein. Example 9 thereof provides for representative expression systems for oncostatin-M using mammalian cells, including CHO cells. In addition, expression from insect cells was described in Example 10 thereof. For the purposes of the invention, all such polypeptide products are within the meaning of the term oncostatin-M.

In addition to the use of oncostatin-M polypeptides prepared or derived as described above, practice of the invention includes also the use of certain other molecules, specifically fragments, mutants, analogs or fusion constructs of oncostatin-M that possess, in whole or part, biological activity thereof.

The nature of these molecules is defined as follows. A "fragment" of oncostatin-M comprises a peptide that contains one or more peptide subsequences from within the pre-propolypeptide of oncostatin-M, whether or not such subsequences are directly adjacent in the primary sequence of oncostatin-M, and may or may not include additional covalently attached groups such as glycosylation. A "mutant" oncostatin-M or mutant fragment thereof comprises an amino acid sequence which when compared to that of oncostatin-M upon which it was patterned, contains for example, one or more deletions, rearrangements, substitutions or insertions of amino acids. A "fusion construct" comprises a polypeptide in which amino acid sequence from oncostatin-M is linked (usually by expression from a fused encoding DNA sequence) to that of another protein. Such a construct contains at least two distinct structural units each providing a desired functionality.

An "analog" of oncostatin-M consists of a molecule which possesses a sufficient amount of the structure of oncostatin-M to be recognized specifically by an antibody directed to an epitope of human oncostatin-M. Additionally, an analog may be represented by a peptidomimetic molecule. Interest in the provision of organic analogs of therapeutic polypeptides began with the recognition that morphine achieves its analgesic effect by mimicking the structure of certain natural peptide analgesics of brain tissue, the endorphins. It is recognized that such organic analogs possess advantages over their polypeptide counterparts including (1) a longer half life before metabolism or nonspecific binding make the natural molecule unavailable; and (2) potentially a lesser likelihood of inducing an immune response in the patient that would limit the utility thereof. General principles are available to guide the synthesis of such analogs. See, for example, Farmer, P.S. Bridging the Gap Between Bioactive Peptides and Drug Design, vol. X, 119–143, Academic Press (1980); Abola, E. E. et al., "Protein Data Bank" in Crystallographic Databases - Information Content, Software Systems, Scientific Applications., Allen, F. H. ed., Data Commission of the International Union of Crystallography, Bonn, pp. 107–132 (1987).

Any of the oncostatin-M polypeptides and molecules of the invention may be utilized in glycosylated or non-glycosylated form.

Representative of such biologically active fragments, mutants, analogs and fusion constructs are the following peptide sequences of oncostatin-M, or molecules:

(a) $Ala^1$-$Arg^{227}$;

(b) a peptide fragment of $Ala^1$-$Arg^{227}$ comprising $Ala^1$-$Arg^{195/196}$;

(c) a peptide fragment of $Ala^1$-$Arg^{227}$ comprising $Ala^1$-$Ser^{185}$;

(d) a mutant peptide fragment of $Ala^1$-$Arg^{227}$ comprising $Ala^1$-$Ser^{185}$ from which amino acid residues $Asp^{87}$ through $Gln^{90}$ are deleted;

(e) a peptide fragment of $Ala^1$-$Arg^{227}$ comprising $Ala^1$-$Ser^{185}$ and containing a $Cys^{49}$ to $Cys^{167}$ disulfide bond;

(f) a peptide fragment of Ala-$Arg^{227}$ comprising $Ala^1$-$Ser^{185}$ and wherein one or more of cysteine residues $Cys^6$, $Cys^{80}$ and $Cys^{127}$ are chemically inactivated or are deleted or replaced separately by one or more amino acids other than cysteine;

(g) a mutant peptide fragment of $Ala^1$-$Arg^{227}$ comprising $Ala^1$-$Ser^{185}$ from which amino acid residues $Thr^{152}$ through $Pro^{155}$ are deleted;

(h) a mutant peptide fragment of $Ala^1$-$Arg^{227}$ comprising $Ala^1$-$Ser^{185}$ wherein the amino acid sequence Gly-Ala-Gly is present between amino acid residues $Leu^{103}$ and $Asn^{104}$;

(i) a mutant peptide fragment of $Ala^1$-$Arg^{227}$ comprising $Ala^1$-$Ser^{185}$ wherein one or both of $Arg^{195}$ and $Arg^{196}$ are replaced by other amino acid residues;

(j) an analog of oncostatin-M comprising a peptidomimetic molecule;

(k) a fusion construct comprising a domain of oncostatin-M primary amino acid sequence and further comprising a domain of interleukin-6 primary amino acid sequence; and (l) a glycosylated form of any of (a) through (k) above.

The above mentioned peptide sequences are representative of those described in Kallestad, J. C. et al. *J. Biol. Chem.*, 266, 8940–8945 (1991) and published International Application No. PCT/US 90/07227, published on Jun. 27, 1991 as International Publication No. WO 91/09057, the text of both documents being incorporated herein by reference. The references disclose mutants of oncostatin-M that retain biological activity. Disclosed thereby (for example at page 10, line 1 to page 11, line 8 of said International Application) are essential functional domains of oncostatin-M, functional peptide sequences, and the identification also of certain mutations that not only preserve but in fact enhance biological activity. Disclosed also therein are deletion, processing, insertion, and substitution mutants of oncostatin-M, and the characterization and expression thereof. Species of peptide sequence described in the aforementioned PCT/US 90/07227 Application as being biologically active are useful in the practice of the present invention.

Additionally, both glycosylated and non-glycosylated forms of such peptide sequences are effective in the practice of the present invention.

There are below described representative clinical indications subject to treatment using the therapeutic compositions of this invention. Such use is applicable also to treatments in veterinary applications, that is, to other mammals. Similarly, oncostatin-M derived from a mammal other than humans, or a biologically active fragment, mutant, analog, or fusion construct thereof comprises "oncostatin-M" within the practice of the invention. Such fragments, mutants, analogs or fusion constructs may be prepared as so described for humans, that is, prepared from natural tissues of a mammal or from cultured cells including recombinant cells, or chemically or enzymatically synthesized.

Potential adverse effects caused by immune response of a veterinary patient to a human-derived therapeutic composition or of a human to a therapeutic composition derived from another mammal species may be ascertained for each individual patient according to standard methodology recognized in the art.

Design of Additional Therapeutic Peptides Patterned on Oncostatin-M

Recombinant genetic techniques allow for the rapid production of and screening of large numbers of mutant oncostatin-M amino acid sequences, or subsequences. As described below such resultant peptides may be tested to determine, for example, their ability to increase TIMP activity, to decrease metalloproteinase activity, to inhibit the invasive behavior of tumor cells, to inhibit inflammation or tissue degeneration, to regulate TIMP activity associated with tissue remodeling or wound repair, or to stimulate TIMP-enhanced erythropoiesis.

A variety of molecular biological techniques are available that can be used to change codons to those encoding other amino acids. Suitable techniques include mutagenesis using a polymerase chain reaction, gapped-duplex mutagenesis, and differential hybridization of an oligonucleotide to DNA molecules differing at a single nucleotide position. For a review of suitable codon altering techniques, see Kraik, C. Use of oligonucleotides for Site Specific Mutagenesis, *Biotechniques*, Jan/Feb 1985 at page 12 thereof.

In the practice of this invention, a preferred method is the site-directed or site-specific mutagenesis procedure of Kunkel, T. A., *Proc. Natl. Acad. Sci. USA*, 82, 488–492 (1985). This procedure takes advantage of a series of steps which first produces, and then selects against, a uracil-containing DNA template. An additional form of site-directed mutagenesis, loop out mutagenesis, may be performed to accomplish deletions following, for example, the procedure of Kramer, et al. *Nucl. Acids Res.*, 12, 9441–9456 (1984).

The above methods are representative of techniques which can be employed to identify within oncostatin-M potentially important primary sequence subdomains or specific amino acids, or mutations of those subdomains or amino acids, that do or could contribute to the biological activity of oncostatin-M. This information can be used to design fragments, mutants, analogs or fusion constructs of oncostatin-M having therapeutic utility.

METHOD 1

Random Mutagenesis to Generate Additional Therapeutic Polypeptides

Using DNA incorporated into a suitable plasmid (encoding for expression in a bacterial construct the amino acid sequence of oncostatin-M) and random mutant oligonucleotides that will span sequentially the entire amino acid sequence of oncostatin-M, novel variant DNA sequences can be constructed which encode variant oncostatin-M-derived polypeptides. Resultant polypeptides expressed therefrom can then be screened for potential therapeutic activity.

Preparation of Oligonucleotides

Mutant oligonucleotides suitable for the mutagenesis protocol and spanning sequential 10 amino acid subdomains of the oncostatin-M polypeptide (for example corresponding to amino acids 100–109, 110–119, 120–129, 130–139) can be generated using a procedure designed to yield a randomly mutagenized oligonucleotide population. Hutchison, C. A. et al., *Proc. Natl. Acad. Sci., USA*, 83, 710–714 (1986). Each randomized oncostatin-M oligonucleotide is then hybridized, for example, using M13mp18 phage (Kunkel, T. A. above) to copy the mutation into an oncostatin-M peptide-encoding DNA sequence.

The resultant mutant M13mp18 populations are then subject to restriction, and the mutagenized DNA sequences are inserted into vectors or plasmids for expression in host bacterial cells following by screening for potential therapeutic activity. Large scale screening of mammalian clones is generally more difficult than for bacterial clones. However, promising mutations identified in bacterial constructs may later be inserted into mammalian or other eucaryotic host cells for further testing or for commercial-scale polypeptide production.

The mutant bacterial clones can be screened for positive results in, for example, an assay measuring enhanced binding of a solubilized and labelled oncostatin-M receptor protein, or fragment thereof. Mutant clones expressing encoded oncostatin-M sequences that exhibit enhanced response in such assays can be sequenced to determine the amino acid alteration(s) responsible for the mutant phenotype. In this way a very systematic analysis of the oncostatin-M molecule can be performed and mutations (and therefore therapeutic peptides containing them) which enhance the biological activity of oncostatin-M can be identified.

METHOD 2

Random Mutation of Targeted Subdomains to Develop Therapeutic Polypeptides

Certain residue positions within the oncostatin-M polypeptide have been identified which when appropriately mutated result in significantly enhanced activity of oncostatin-M in certain assays. For example, deletion of the sequence $Asp^{87}$ to $Gln^{90}$, results in a polypeptide having enhanced biological activity, Kallestad, J. C. *J. Biol. Chem.*, 266, 8940–8945 (1991). Accordingly, random mutagenesis of the DNA corresponding to the important amino acid subsequence directly adjacent to the $Asp^{87}$-$Gln^{90}$ site, for example, could be emphasized.

Additionally, biologically active fragments, mutants, analogs and fusion constructs of oncostatin-M including glycosylated and non-glycosylated forms of the aforementioned peptides can be produced by enzymatic synthesis or chemical synthesis, such methods being known in the art. A method of chemical synthesis, particularly adapted to synthesis of peptides of less than about 100 amino acid residues in length is that of Houghten, R. A. et al., *Proc. Natl. Acad. Sci. USA*, 82, 5135, (1985).

Therapeutic Oncostatin-M Compositions Involving Additional Cytokines

Therapeutic compositions comprising oncostatin-M, or a biologically active fragment, mutant, analog or fusion construct thereof may be prepared that comprise also certain additional cytokines.

Transforming growth factor-β (including, for example, the $\beta_1$ form thereof) has been demonstrated to increase expression of TIMP in human fibroblasts when used in combination with polypeptide growth factors such as EGF. Edwards, D. R., et al., *The EMBO Journal*, 6(7), 1899–1904 (1987), Overall, C. M., et al., *J. Biol. Chem.*, 264(3), 1860–1869 (1989). Certain fibroblast cell lines have also been identified for which TGF-β alone induced increased secretion of TIMP. Wright, J. K., *Biochemica et Biophysica Acta*, 1094, 207–210 (1991).

It has also been established that administration of TGF-β to fibroblast cultures results in inhibition of synthesis of collagenase, MMP-1 (Edwards, D. R., et al., supra) and also of stromelysin, MMP-3 (Matrisan, L. M., et al., *Moll. Cell Biol.*, 6, 1679–1686 (1986). Accordingly, therapeutic compositions comprising oncostatin-M (or a biologically active fragment, mutant, analog or fusion construct thereof) and TGF-β are useful in the practice of the invention where inhibition of activity of the above mentioned metalloproteinases is desired. In one study, TGF-β stimulated production of (pro)gelatinase (Overall, C. M., et al., supra) and this may limit its utility.

Preferable also are therapeutic compositions that comprise oncostatin-M (or a biologically active fragment, mutant, analog or fusion construct thereof) and interleukin-6 or leukemia inhibitory factor. In Example 2 (see also FIG. 2) of the invention it is demonstrated that although interleukin-1a stimulates expression of TIMP protein, it stimulates also expression of (pro)collagenase. However, under the conditions tested, interleukin-6 and leukemia inhibitory factor stimulated expression of TIMP protein without affecting collagenase expression. Interleukin-6 and leukemia inhibitory factor failed also to stimulate stromelysin expression (FIG. 3, and Example 3 below). Accordingly, therapeutic compositions comprising oncostatin-M and one or more of interleukin-6, TGF-β and leukemia inhibitory factor are useful in the practice of the invention in that they inhibit net metalloproteinase activity by upregulating TIMP expression but not affecting metalloproteinase expression.

TIMP Proteins Affected by Oncostatin-M Administration

"TIMP" according to the practice of the invention includes the protein species known as TIMP-1 and TIMP-2 and includes (A) any related peptide having immunological cross reactivity or amino acid sequence homology to said TIMP-1 or TIMP-2, or (B) any related peptide that is capable of combining with one or more species of metalloproteinase, whether in proenzyme or activated form, thereby forming a complex in which the metalloproteinase is substantially deactivated or prevented from becoming active. By immunological cross reactivity it is meant that one or more antibodies produced in response to a "TIMP" will bind specifically to a common epitope of naturally occurring human TIMP-1 or TIMP-2, or that one or more antibodies produced specifically in response to TIMP-1 or TIMP-2 will bind also to a common epitope of the additional TIMP protein.

The amino acid sequence of TIMP-1 has been determined and the protein has been expressed from recombinant bacterial and mammalian host cells. See Docherty, A. J. P. et al. *Nature*, 318, 66–69 (1985). TIMP-1 has been purified from a number of source tissues including amniotic fluid, synovial fluid, saliva, bone, tendon, and from culture medium conditioned by fibroblasts or osteoblasts. As mentioned previously, TIMP-1 is a glycoprotein of apparent molecular weight of approximately 28.5 kDa with an apparent core polypeptide weight of about 21 kDa.

TIMP-2 was described by Stetler-Stevenson, W. G. et al. *J. Biol. Chem.* 264(29), 17374–17378 (1989) as a nonglycosylated protein of approximate 21 kDa molecular weight that also forms 1:1 complexes with certain metalloproteinases and that is found in human tissue. TIMP-1 and TIMP-2 share substantial amino acid sequence homology including conservation of 12 cysteine residues believed to form 6 important disulfide bonds that define, in part, the structure for TIMPs. TIMP-2 was also independently isolated as "metalloproteinase inhibitor" from bovine aortic endothelial cells, Boone, T. C. et al. *Proc. Natl. Acad. Sci. USA*, 87, 2800–2804 (1990). The bovine and human forms of TIMP-2 contain amino acid sequences that are about 90% identical. TIMP-1 is known to be identical with independently discovered EPA protein (erythroid-potentiating activity). Gasson, J. C. *Nature*, 315, 768–771 (1985).

There has also been identified from cultured human fibroblasts an additional metalloproteinase inhibitor protein, "LIMP" - large inhibitor of metalloproteinase. Cawston, T. E. et al. *Biochem. J.*, 269, 183–187 (1990). LIMP is known to inactivate metalloproteinase by complexing therewith. Accordingly, it is predicted that administration to a patient of oncostatin-M will affect LIMP activity in a manner similar to TIMP activity. This prediction may be verified according to the procedures described herein for assay of TIMP activity or metalloproteinase activity.

TIMP and/or TIMP activity can be assayed according to the procedures of Examples 1 through 4 below, or, for example, by the procedures of Cawston, T. E. et al., cited above, and Overall, C. M. et al., *J. Biol. Chem.*, 264, 1860–1869 (1989). See also Firestein, G. et al. *Arthritis & Rheumatism*, 34, 1094–1105 (1991) concerning determination of TIMP mRNA expression in situ.

Metalloproteinase Activity

Metalloproteinases are enzymes that digest protein components of extracellular matrix. Metalloproteinases are of central importance to (1) the invasive or metastatic behavior of tumor cells, (2) the progression of inflammatory and degenerative diseases, and (3) to processes of tissue remodeling or regeneration (such as wound healing) that involve changes in extracellular matrix. There follows hereafter a description of specific metalloproteinases and of the involvement of metalloproteinase in the above-described processes. From the following discussion it will be seen that above-described processes (1), (2) and (3) are interrelated.

A description of metalloproteinases and their role in metastasis and other invasive or degenerative processes is provided by Khokha, R. and Denhardt, D. T. *Invasion Metastasis*, 9, 391–405 (1989). Mammalian metalloproteinases comprise a family of enzymes that typically cleave internal peptide bonds of target proteins instead of a terminal peptide bond, that typically require calcium ions for activity, typically contain tightly bound zinc ions, and usually have optimal activity at or near neutral pH. In order to maintain control over unintended tissue degradation, metalloproteinases are secreted typically as inactive proenzymes that require activation to generate the catalytic form. For the purpose of the invention, "metalloproteinases" are also defined as proteinases possessing immunological cross reactivity or active site amino acid sequence or structural homology with any of the below-mentioned species of proteinase.

Representative metalloproteinases include: (A) interstitial collagenase, also referred to as type-1 collagenase, matrix metalloproteinase I or "MMP-1"; (B) type-IV collagenase, also referred to as 72,000 (72 kDa) molecular weight gelatinase or "MMP-2"; (C) stromelysin, also referred to, for example, as stromelysin-1, proteoglycanase, transin, or "MMP-3"; (D) 95,000 (95 kDa) molecular weight gelatinase or "MMP-9"; stromelysin-2 or "MMP-10"; stromelysin-3; PUMP-1 or "MMP-7"; and PMN collagenase or "MMP-8". The above metalloproteinases are representative of a family of enzymes with individual but often overlapping specificities for particular target extracellular matrix macromolecules.

Numerous of the aforementioned species contain partially conserved functional domains and amino acid sequences. Docherty, A. J. P. and Murphy, G. *Annal. Rheumatic. Dis.*, 49, 469–479 (1990) identify a "domain 2" within metalloproteinases as the active site thereof. In comparing five metalloproteinases (MMP-1, MMP-2, MMP-3, MMP-9 and MMP-10), domain 2 showed regions of striking amino acid sequence conservation that may explain also the affinity of TIMP for each of these metalloproteinases. There is hereafter provided certain information concerning the target specificity of metalloproteinases.

Collagens are a group of fiber-forming proteins found in all animals and that comprise about 20% of the weight of all protein therein. Collagens are formed into unique structures in which three polypeptide chains wind around each other to form triple helices. There are several types of component polypeptides leading to several types of triple stranded collagen. As is well known in the art, types I, II and III collagen are the main forms found in connective tissue, with type I being the most common. Type IV collagen is the most common form of collagen found in basal laminae. Type V collagen is widely distributed in nearly all matrix structures but in small amounts. Collagenous fibers confer great tensile strength on the tissues or structures in which they are located.

Another component of extracellular matrix, particularly in connective tissue, is the protein elastin which is typically present as a network of elastic fibers that confer on the structures in which they are positioned the capability to recover from stretching. Typically extracellular matrix structure contains (inelastic) collagen fibers interwoven with elastin to prevent tearing of tissue.

Large aggregates of the protein fibronectin also exist in the extracellular matrix. There is substantial evidence that metastatic or invading tumor cells make little fibronectin and that they can be converted to a somewhat more normal phenotype (acquiring for example the typical flattened appearance of adhering non-tumor cells) by adding fibronectin to the culture. Degradation of fibronectin under some circumstances is believed to promote metastasis.

The polysaccharide components of glycosaminoglycans (proteoglycans) are less able to form folded globular structures than most proteins, consequently these macromolecules are required to adopt very extended, hydrated structures that fill the entirety of the extracellular space. The structural ordering of proteoglycan, collagen, elastin and fibronectin is important to the functioning of the matrix. There is substantial evidence also that metabolism of hyaluronic acid (a common type of glycosaminoglycan) is important to facilitate cell migration during tissue repair.

The metalloproteinases, in combination, are able to degrade all of the aforementioned matrix components. For a review of metalloproteinase substrate specificity see Docherty, A. J. P. and Murphy, G. *Annals of the Rheumatic Diseases*, 49, 469–479 (1990). Of particular note, type-1 collagenase (MMP-1) specifically targets Gly-Leu and Gly-Ileu bonds in the helical structure of types I, II and III collagen. 72,000 molecular weight gelatinase (MMP-2) has been demonstrated to degrade collagen types IV and V. Stromelysin (MMP-3) has been demonstrated to degrade laminin, type IV collagen, fibronectin, and the proteinaceous core of proteoglycans.

Additionally, a component of macrophage elastase activity has been identified as having stromelysin-like character, Werle, Z. and Gordon, S. *J. Exp. Med.*, 142, 361–377 (1975), Banda, M. and Werb, Z. *Biochem. J.*, 193, 589–605 (1981). This proteinase activity has been implicated in tissue destruction (elastin component) associated with the progression of emphysema and atherosclerosis. Inhibition of macrophage elastase (via oncostatin-M mediated enhancement of TIMP activity) comprises a therapy to inhibit the progression also of these two diseases.

Metalloproteinase concentrations or metalloproteinase activities can be assayed according to the procedures of Examples 2 and 3 below or, for example, by the following procedures. For MMP-1: type 1 collagenase can be measured by monitoring degradation of [$^{14}$C] glycine-labelled soluble collagen, Overall, C. et al., *J. Biol. Chem.*, 264, 1860–1869 (1989), or of [$^3$H] acetylated collagen, Cawston, T. E. and Barrett, A. *Anal. Biochem.*, 99, 340–345 (1979). For MMP-2: 72 kDa gelatinase can be measured by monitoring degradation of [$^{14}$C] glycine-labelled gelatin, Overall, C. and Sodek, J. *J. Dent. Res.*, 66, 1271–1282 (1987), or of

[³H] acetylated gelatin, Murphy, G. et al., *Biochem. J.*, 199, 807–811 (1981), or by the method of gelatin-substrate enzymography, Overall, C. et al. (1989) as cited directly above. For MMP-3: stromelysin can be measured by monitoring degradation of [³H] acetylated casein, Cawston, T. et al. *Biochem. J.*, 269, 183–187 (1990) and Murphy, G. et al. (1981) as cited directly above. Other procedures are known in the art.

Clinical Indications Subject to Treatment with the Therapeutic Compositions of the Invention
Invasive and Metastatic Potential of Tumor Cells Metalloproteinase activity is of particular importance to the behavior of malignant (invasive) tumor cells, that is, cells which differ from benign tumor cells in that they possess the ability to penetrate the basement membrane of the tissue of origin and/or to give rise to metastasis at sites different from the primary tumor.

Successful treatment of tumors that have metastasized is difficult. Even if a therapeutic program kills 99.9% of such cells, the remaining 0.1% are free to colonize new tissues or organs throughout the body, penetrating their structures and disrupting the function thereof. Consequently preventing or inhibiting substantially the invasive or metastatic potential of tumor cells is of great clinical importance.

Metastasis is a complex process that involves a series of steps, many of which involve degradation of extracellular matrix. Typically, malignant tumor cells break away from the primary tumor in a particular tissue, penetrate any surrounding tissues, penetrate also the basement membrane surrounding adjacent blood or lymph vessels thereby entering the circulatory system (the process of intravasation) and may then be transported to distant sites. In order to successfully metastasize at a new site, the tumor cells must extravasate from the circulatory system, again by a process of degrading extracellular matrix.

The production by tumor cells of collagenases provides a means of proteolyzing collagens, the principal component of extracellular matrix. A variety of human tumors have been reported to have substantial collagenolytic capability. See, for example, Abramson, M. et al. *Ann. Otol.*, 84, 158–163 (1975), Yamanishi, Y. et al. *Cancer Res.*, 32, 2551–2560 (1972), Yamanishi, Y. et al. *Cancer Res.*, 33, 2507–2512 (1973) and Hashimoto, K. et al. *Cancer Research*, 33, 2790–2801 (1973). With respect to stromelysin, see Matrisian et al. *Proc. Natl. Acad. Sci. USA*, 83, 9413–9417 (1986); Basset et al. *Nature*, 348, 699–704 (1990). A variety of other tumors have been reported that have substantial levels of activity of other metalloproteinases.

It is noted that the high level of metalloproteinase activity in metastatic tumors (and that may be decreased according to the practice of the invention) need not be produced by the tumor itself, but may be induced by the tumor cells in normal cells of the adjacent connective tissue, such as fibroblasts. For example, Biswas, C. and Gross, J. *J. Cell Biol.*, 91, 163a (1981) have demonstrated that culturing normal rabbit fibroblasts with either mouse melanoma cells or adenocarcinoma cells produces substantial type I collagenase activity whereas none of these cell types, if cultured separately produced detectable activity. It is likely that the fibroblasts were the source of collagenase and that the tumor cells provided an inducer since conditioned (but cell free) medium from the cultured tumor cells also induced collagenase activity in the fibroblasts.

Arthritic Disease

There is substantial evidence that imbalance between the level of proteinase activity and anti-proteinase activity in cartilaginous tissue is responsible for many of the degenerative symptoms of rheumatoid arthritis and osteoarthritis.

Rheumatoid arthritis is a chronic inflammatory disease primarily of the joints that may result in permanent loss of joint function. Irreversible loss of joint function is attributed to severe degradation of collagen and degradation also of bone, ligament and tendon. Associated chronic inflammation results in part from immune response at the affected joint, although the exact nature of the triggering antigens is unknown. The immune response may be autoimmune in origin. Mullins, D. E. and Rohrlich, S. T. *Biochemica et Biophysica Acta*, 695, 177–214 (1983) at 192–193 thereof describe the etiology of the disease in detail. Briefly there is a progressive loss of cartilage (a connective tissue) caused by invading cells. Both collagen and proteoglycan components of the cartilage are degraded by enzymes released at the affected site.

The combined results of numerous studies directly implicate MMP-1 type metalloproteinase in the degradation of cartilage associated with rheumatoid arthritis. See, for example, Wooley, D. E. et al. *Arthritis Rheum.*, 20, 1231–1239 (1977), Wooley, D. E. et al. in *Collagenase in Normal and Pathological Connective Tissues*, (Wooley, D. E. and Evanson, J. M. eds.), pp. 105–125, John Wiley & Sons, New York, N.Y. (1980). Gelatinase-type metalloproteinase is also likely involved, Harris, E. D., Jr. et al. in *Immunopathology of Inflammation*, Forscher, B. K. and Houck, J. C., eds. pp. 243–253, Excerpta Medica, Amsterdam (1971).

Although the permanent damage to a joint caused by rheumatoid arthritis involves many factors and a series of events, the concentration of metalloproteinase inhibitors, such as TIMP, at the affected site is simply inadequate to inactivate the concentration of metalloproteinase that is present.

Osteoarthritis is an additional type of arthritic disease characterized by the degradation of articular cartilage with concomitant degradation of collagen and proteoglycan components thereof. Evidence for excess of metalloproteinase activity at joints affected by osteoarthritis is substantial. See, for example, Pelletier, Jean-Pierre et al. *Arthritis and Rheumatism*, 26(7), 866–874 (1983). Total metalloproteinase activity has been determined to be elevated three- to tenfold in osteoarthritis-affected cartilage. Martel-Pelletier, J. et al. *Arthritis and Rheumatism*, 27(3), 305–312 (1984).

Dean, D. D. et al. *J. Clin. Invest.*, 84, 678–685 (1989) have also demonstrated that in human osteoarthritic cartilage the normal balance between metalloproteinase activity and TIMP activity is upset, leading to a net excess of metalloproteinase activity.

Both osteoarthritis and rheumatoid arthritis may be treated by methods effective to raise the level of TIMP activity at an affected site. This is accomplished according to the practice of the present invention by administration of therapeutic compositions (including, for example, injection at an affected joint) comprising oncostatin-M or a biologically active fragment, mutant, analog or fusion construct thereof.

Inflammation

Inflammation occurs in response to numerous conditions including, but not limited to, physical injury, tumor growth in a tissue, chemical damage to a tissue, and bacterial, parasitic or viral infection. Inflammation results in both local and systemic effects. Representative of effects that can occur at a site of injury or disease are increased vascular permeability, release of degradative enzymes including metalloproteinase (from several sources including migrating macrophages), migration to the affected site by leukocyte cells, neutrophil burst response to destroy invading cells, and the secretion of cytokines. Important systemic effects include pain, fever, and the acute phase response of the liver which involves (as elaborated below) the release, for example, of antibacterial proteins and of a wide spectrum of proteinase inhibitors.

The above processes are responsible substantially for the degradation of damaged tissue and for inactivating causative agents of the inflammation such as invading bacteria. However, the arsenal of cells and enzymes, such as proteinases, that are committed to inactivating the foreign entity must be closely regulated. The potential for proteolytic degradation of healthy self-cells and self-proteins is very high. Accordingly, the acute phase response of the liver involves also the production of a broad spectrum of protective substances. See, for example, Fey, G. H. and Fuller, G. M., *Mol. Biol. Med*, 4, 323–338 (1987), and Schreiber, G. "Synthesis, Processing and Secretion of Plasma Proteins by the Liver and Other Organs and Their Regulation" in *The Plasma Proteins*, Putnam, F. W., ed., Vol. 5, Academic Press, New York, N.Y. (1987).

Certain of acute phase proteins facilitate removal of foreign particles, immune complex particles, and microorganisms. As described by Fey, G. H. and Gauldie, J., *The Acute Phase Response Of The Liver In Inflammation*, in Progress in Liver Diseases, Popper, H. and Schaffner, S. eds., vol. 9, Chapter 7, pp. 89–116, W. E. Saunders Co. (1990), many of the acute phase proteins are proteinase inhibitors. Representative thereof are $\alpha_1$-proteinase inhibitor; $\alpha_1$-antichymotrypsin; $a_2M$-, $\alpha_1 I3$-, and $\alpha_1$-macroglobulins; and $\alpha_1$ major acute phase protein.

It has been demonstrated also that numerous cytokines regulate expression of hepatocyte gene expression. See, Fey, G. H. and Gauldie, J., supra; Richards, C. D. et al., *Eur Cyt. Net*, 2(2), 89–98, (1991), and U.S. Pat. No. 4,973,478 to J. Gauldie and C. Richards. The list of cytokines capable of facilitating response to inflammation includes interleukin-6, interleukin-11, interleukin-1$\alpha$, tumor necrosis factor and leukemia inhibitory factor.

As described in detail by Richards, C. D. et al., *The Journal of Immunology*, 148, 1731–1736, issue of Mar. 15, 1992, which is not prior art to the present invention and which is incorporated herein by reference, oncostatin-M has potent acute phase protein-inducing activity for hepatocytes. Doses of oncostatin-M suitable for administration to patients in therapeutic compositions to stimulate acute phase response are predicted to range from about 0.05 to about 5 mg/patient per day.

Accordingly, a broad spectrum of disease states or injuries that result in either inflammatory response or tissue degeneration at an afflicted site may be treated (or at least the severity of symptoms thereof can be limited) by administration of therapeutic compositions comprising oncostatin-M or biologically active fragments, mutants, analogs or fusion constructs thereof. Additional clinical circumstances for which such therapeutic compositions are indicated include (A) conditions such as diabetic retinopathy (see below) where treatment of an undesired pattern of angiogenesis is needed, (B) periodontal disease, and (C) other disease states involving tissue degeneration and/or inflammation including emphysema, atherosclerosis, and pneumonia of viral, bacterial or chemical origin.

Clinical Conditions Involving Angiogenesis

Angiogenesis refers to the production of new blood capillaries caused by cell migration and proliferation from existing capillaries. The process is recognized in the art to be somewhat similar to metastasis in that capillary wall endothelial cells must migrate through the basement membrane of the parent capillary. As noted by Mullins, D. E. and Rohrlich, S. T., supra, at 191, "Angiogenesis is important in a number of physiological conditions, both normal and pathological, including vascularization of granulation tissue during wound healing, vascularization during embryological development and tissue growth, and vascularization of grafts. In diabetic retinopathy, the abnormal proliferation of capillaries may lead indirectly to retinal detachment and blindness."

There is considerable evidence that the initial events of angiogenesis require the presence of degradative enzymes such as metalloproteinase. Rohrlich, S. T. and Rifkin, D. B. in Annual Reports in Medicinal Chemistry, Hess, H-J., ed., 14, pp. 229–239, Academic Press, New York, N.Y. (1979).

Accordingly, regulating the level of TIMP activity at a site undergoing angiogenesis would be of great clinical utility in the control of capillary development. Such regulation can be accomplished using the therapeutic compositions of the invention. With respect to preventing retinal detachment associated with diabetic retinopathy, oncostatin-M, or a biologically active fragment, mutant, analog or fusion construct thereof can be administered so as to inactivate at least a substantial fraction of all metallproteinase available at the appropriate site in the eye. With respect to regulating a desired physiological process such as the controlled and proper vascularization of a tissue graft, oncostatin-M derived therapeutic compositions can be administered to downregulate the rate of vascularization by inactivating only a fraction of the metalloproteinase present.

As described above, metabolism or morphological alteration of extracellular matrix is important to many normal and pathological processes. Further evidence of the importance of extracellular matrix is based on the recognition that tumor development requires effective angiogenesis, that is, growth of the tumor is dependent on the development of capillaries to provide nutrients, said capillaries serving also as an exit pathway for metastasis-capable cells. The broad utility of the present invention in regulating metalloproteinase activity is thus underscored.

Periodontal Disease

Periodontal (surrounding or involving the teeth) disease is a localized inflammatory and degenerative condition involving the gums (gingivitis) and/or periodontal ligament and the alveolar bone that supports the teeth (periodontitis). Dental plaque comprises bacteria that adhere tightly to the tooth surfaces. The presence of plaque causes inflammation of the gums and, in periodontitis, loss of attachment between the gums and the affected teeth. Bone loss may be apparent also.

Periodontitis involves both attack by bacterial protease and also the collateral consequences of the response of the patient's immune system to the plaque. For a review of involved processes, see Greenspan, J. S. and Boackle, R. J., "Oral and Dental Diseases" in *Basic and Clinical Immunology*, Chapter 42, Fudenberg, H. H. et al., eds., 3rd ed., Lange Publishers, Los Altos, Calif. (1980). Host inflammatory response to the invading bacteria includes production of metalloproteinase leading to tissue degradation. Accordingly, periodontal disease may be treated as described below, according to the practice of the invention, using therapeutic compositions comprising oncostatin-M, or a biologically active fragment, mutant, analog, or fusion construct thereof.

Tissue Remodeling and Healing of Wounds

Remodeling and repair of tissue are related to invasive diseases such as rheumatoid arthritis and metastatic cancer in that there is involved the modulation of breakdown of extracellular matrix. It is apparent that without proper regulation of matrix macromolecule metabolism during remodeling or repair, damage to the target tissue would become severe. Representative examples of tissue remodeling include post-partum involution of the uterus and post-lactation involution of the breast. See Mullins, D. E. and Rohrlich, S. T. *Biochemica et Biophysica Acta,* 695, 177–214 (1983) for a general discussion thereof. Uterine involution is caused in substantial part by the activity of a neutral collagenase (MMP-1). Woessner, J. F., Jr., in *Collagenase in Normal and Pathological Connective Tissues* Woolley, D. E. and Evanson, J. M. eds. at pp. 223–239, John Wiley and Sons, New York, N.Y. (1980).

Healing of injury is closely related to the aforementioned processes in that it involves tissue remodeling and also migration of cells. Various types of cells including fibroblasts and epithelial cells migrate into or across a wound during the healing process. For example, fibroblasts secrete new collagen and other matrix macromolecules between cells at the wound site, a significant portion of said molecules being resorbed during later stages of wound repair. Collagenase activity is thus strongly implicated. Grillo, H. C. and Gross, J. *Dev. Biol.,* 15, 300–317 (1967).

Remodeling of tissue such as occurs during healing of burns may also be modulated by administration to the afflicted patient of oncostatin-M, or a biologically active fragment, mutant, analog or fusion construct thereof.

Of particular importance to the practice of the present invention is the phenomenon of persistent epithelial defect, that is, incomplete healing and/or ulceration of a wound site. Such incomplete healing is often resistant to treatment and may result in permanent impairment of function, as in a damaged cornea. Representative of undesired processes or results associated with persistent defects (unhealed wounds) are degradation of basement membrane and presence of excessive collagenase proteinases. See, for example, Bergman, M. B. in *Collagenase in Normal and Pathological Connective Tissues,* Woolley, D. E. and Evanson, J. M. eds., at pp. 141–174, John Wiley and Son, New York, N.Y. (1980), Pfister, R. R. and Burnstein, N. *Exp. Eye Res.,* 23, 519–535 (1976), and Slansky, H. H. and Dohlman, C. H. *Surv. Opthamol.,* 14, 402–416 (1970).

Although many macromolecules and circumstances contribute to the state of incomplete healing of tissues, representative of such circumstances are excess collagenase production and degradation of basement membrane leading to a state of an inadequate scaffolding on which to effect proper repair. Therapeutic compositions of the invention are effective to terminate a state of incomplete healing by making, in general, increased TIMP available to inactivate metalloproteinases.

Accordingly, the therapeutic compositions of the invention can be used effectively to modulate the repair or remodeling of tissues.

Stimulation of Erythropoeisis by Oncostatin-M

There are numerous circumstances when it is desirable to stimulate the production of red blood cells in a patient. A shortage of red blood cells may occur, for example, following burns, hemorrhage or as a result of chemotherapy, cancer, viral infection or exposure to radiation. Additionally there are various red cell disorders in which immune processes play a very important role. Representative of such disorders are immune hemolytic anemias, aplastic anemia, and hemolytic disease of the newborn resultant from placental crossover of maternal antibody.

As mentioned previously, TIMP-1 protein was determined (Docherty, A. J. P. et al. *Nature,* 318, 66–69 (issue of Nov. 7, 1985)) by sequence analysis to be identical with a protein identified previously as erythroid-potentiating activity ("EPA"), Gasson, J. C. *Nature,* 315, 768–771 (issue of Jun. 27, 1985). That "EPA" type activity (the ability to stimulate proliferation and further maturation of erythroid progenitor cells) is present in purified TIMP-1 has been confirmed, Hayakawa, T. et al., *FEBS Letters,* 268(1), 125–128 (1990), using TIMP-1 expressed from human bone marrow fibroblastoid stromal cells, KM-102.

TIMP-1 has been demonstrated to stimulate the growth of erythrocyte precursor cells (Westbrook, C. A. et al. *J. Biol. Chem.,* 259, 9992–9996 (1984)), and also of human erythroleukemia cells (Avalos, B. R. et al., *Blood,* 71, 1720–1725 (1988)).

According to the practice of the present invention, an important clinical use for therapeutic compositions comprising oncostatin-M, or biologically active fragments, mutants, analogs or fusion constructs thereof, comprises stimulating erythropoiesis in accord with the ability of oncostatin-M to increase TIMP activity and the concentration of TIMP in a patient. It is known that erythroid progenitor cells are found in the bone marrow in close contact with cells that produce certain growth factors therefor. A principal discovery of the invention is the demonstration that bone marrow stromal cells (see Example 8) produce TIMP-1 in response to stimulation with oncostatin-M. TIMP-1 secreted from these cells is expected to be available directly to the progenitor cells. Oncostatin-M administered to patients to stimulate the production of mature erythrocytes can be administered, for example, by injection, including at sites in the marrow.

Oncostatin-M therefor may also be administered in conjunction with other compounds known to have erythropoietic effects, for example, insulin-like growth factor, cyclic AMP, and prostaglandins. In addition to acting by increasing TIMP activity, oncostatin-M is believed also to act directly to stimulate proliferation and further maturation of erythroid progenitor cells.

It is noted also that current research (Hayakawa, T. et al. *FEBS Letters,* 298(1), 29–32 (1992)) indicates that: TIMP-1 is a "fundamental and ubiquitous protein in human beings"; that TIMP-1 "has potent growth factor-promoting activity for other cells besides erythroid precursor cells"; and that TIMP-1 likely represents "a new cell-growth factor in serum" (all at p. 29 thereof). Accordingly stimulation of growth of a wide range of mammalian cell types, whether in vivo or in vitro, and production therein or therefrom of a wide variety of pharmaceutically-useful biomolecules is expected to be made practical by oncostatin-M enhanced, TIMP-mediated processes.

Additional Indications

The following disease states can also be treated according to the practice of the invention since underlying inflammatory and degenerative mechanisms associated with the pathology thereof involve metalloproteinases: emphysema, atherosclerosis, and pneumonia (whether of bacterial, viral or chemical origin).

Therapeutic Compositions and Administration Thereof

Oncostatin-M, or a biologically active fragment, mutant, analog or fusion construct thereof is formulated into pharmaceutical preparations for therapeutic use. To prepare such molecules for intravenous administration, for example, they are dissolved in water preferably containing physiologically compatible substances such as sodium chloride, glycine, and the like, the resultant solution having a pH compatible with administration to patients, said water or water with physiologically compatible substances comprising a pharmaceutically acceptable carrier.

The amount of oncostatin-M to administer for the prevention or inhibition of inflammatory or degenerative disease, to inhibit the invasive or metastatic potential of tumor cells, to stimulate erythropoiesis, or to regulate tissue remodeling or healing of injury can be determined readily for any particular patient according to recognized procedures.

The therapeutic compositions may be used in the treatment of a wide variety of cancers such as carcinomas, sarcomas, melanomas and lymphomas and which may affect a wide variety of organs, including, for example, the lungs, mammary tissue, prostate gland, small or large intestine, liver, heart, skin, pancreas and brain. The therapeutic compositions may be administered to patients in the case of treatment of tumors, for example, by injection (intravenously, intralesionally, peritoneally, subcutaneously), or by topical application and the like as would be suggested according to the routine practice of the art.

Therapeutic compositions useful to inhibit the invasive and/or metastatic potential of tumor cells may be administered typically in conjunction with other therapies, such as chemotherapy that affects directly the growth and proliferation of cells in existent tumor masses. With respect to the treatment of a large percentage of patients, by the time diagnosis of an initial malignant growth is made, metastasis has already likely occurred. Accordingly a preferred method for inhibiting or treating the progression of cancer in a patient comprises administration of oncostatin-M in conjunction with a program to administer chemotherapeutic agents.

For use in the treatment of inflammatory or degenerative conditions the therapeutic compositions are best administered by injection at the affected site, by aerosol inhalation (as in the case of emphysema or pneumonia), or by topical application or transdermal absorption as would also be suggested according to the routine practice of the art. Specific inflammatory or degenerative conditions that may be treated with oncostatin-M or with molecules of the invention patterned thereon include rheumatoid arthritis, osteoarthritis, periodontal disease, diabetic retinopathy, emphysema, atherosclerosis, and pneumonia (whether of viral, bacterial or chemical origin).

The therapeutic compositions of the present invention may be used also for treating a wide variety of wounds including substantially all cutaneous wounds, corneal wounds, and injuries to the epithelial-lined hollow organs of the body. Wounds suitable for treatment include those resulting from trauma such as burns, abrasions, cuts, and the like as well as from surgical procedures such as surgical incisions and skin grafting. Other conditions suitable for treatment with the compositions of the present invention include chronic conditions, such as chronic ulcers, diabetic ulcers, and other non-healing conditions.

As described above, oncostatin-M and molecules of the invention patterned thereon may be incorporated into pharmaceutically-acceptable carriers for application to the affected area. The nature of the carrier may vary widely and will depend on the intended location of application and other factors well known in the art. For application to the skin, a cream or ointment base is usually preferred, suitable bases including lanolin, Aquaphor (Duke Laboratories, South Norwalk, Conn.), Silvadene (Marion) particularly for the treatment of burns, and the like.

An additional method whereby the therapeutic compositions of the invention can be formulated comprises incorporation thereof into the lumen of liposomes.

If desired, oncostatin-M containing compositions can be incorporated into bandages and other wound dressings to provide for continuous exposure of the wound to the therapeutic molecules. Aerosol applications are also useful. Additionally, the compositions can be applied topically to the affected area, typically as eyedrops to the eye or as creams, ointments or lotions to the skin. In the case of eyes, frequent treatment is desirable, usually being applied at intervals of a few hours or less. On the skin, it is desirable to continually maintain the treatment composition on the affected area during healing, with several applications of the treatment composition per day being preferred usually. Therapeutic compositions of the invention can be used also to stimulate acute phase response by the liver to inflammation or to stimulate erythropoiesis. In such cases the compositions are preferably administered by injection.

As described above, additional therapeutic substances have been determined to increase TIMP activity and/or decrease metalloproteinase activity. Therapeutic compositions can be formulated containing oncostatin-M and such other substances, for example, estrogens, progesterone, retinoid compounds, glucocorticoids, and additional cytokines such as, for example, interleukin-6, leukemia inhibitory factor, and transforming growth factor β. It is very likely that oncostatin-M can be similarly formulated with additional of such substances whose ability to increase TIMP activity remains to be discovered.

TIMP-1 expression has also been shown to be upregulated in vitro by the cytokines tumor necrosis factor and epidermal growth factor. It is within the practice of the invention to treat any of the clinical indications described herein with one or more therapeutic compositions containing either of these cytokines and also oncostatin-M.

Finally, since TIMP is itself a therapeutically useful substance, it is desirable to produce commercially useful quantities of TIMP in vitro such as from cultures of recombinant cells containing TIMP-encoding DNA. Contacting such cells (having particular and predetermined capacity to produce TIMP under particular conditions of cell culture) with oncostatin-M or a biologically active fragment, mutant, analog or fusion construct thereof, stimulates the recombinant cells to produce TIMP in excess of predetermined capacity. TIMP for therapeutic or diagnostic use may therefore be made available more efficiently and economically.

EXAMPLES

The following Examples are representative of the practice of the invention.

Example 1

Stimulation of TIMP-1 Protein Expression in Human Lung Fibroblasts

Culturing of fibroblasts

For the purpose of this Example, cultures of non-transformed human fibroblasts were obtained from normal lung tissue according to the method of Jordana, M. et al. *Am. Rev. Rest. Dis.*, 137, 579–584 (1988). Similar results were obtained using human synovial fibroblasts. Cells were seeded from a concentration of $5 \times 10^5$/ml into 6-well cluster plates, 35 mm diameter, Corning Glass Works, Corning, N.Y., in Dulbecco's modified Eagle's medium ("DMEM") (Gibco/Life Technologies, Inc., Gaithersburg, Md.) supplemented with 10% heat-inactivated fetal bovine serum ("FBS"). Confluence was achieved after 72–96 hours of growth at 37° C. in a 5% $CO_2$ atmosphere. The confluent cell samples were then maintained with DMEM supplemented with 2% (v/v) of heat-inactivated FBS (Gibco/Life Technologies, Inc.), and then maintained at 37° C. in a 5% $CO_2$ atmosphere in the presence of human oncostatin-M for a period of 18 hours. The effect of oncostatin-M was tested at final concentrations thereof of 1, 10, 20 and 50 ng/ml (see FIG. 1). Human recombinant oncostatin-M was delivered from a stock solution of 1 mg/ml oncostatin-M, 40% acetonitrile (v/v), 0.1% (w/v) trifluoroacetic acid in phosphate buffered saline ("PBS," 146 mM NaCl, 20 mM $K_2H$ and $KH_2PO_4$), final pH 7.4. See Malik, N. et al. *Mol. Cell. Biol.*, 9, 2847–2853 (1989). Stock solutions of this type may be maintained for greater than 1 year at −20° C. without significant deterioration as measured in radioreceptor binding and target cell growth inhibition assays.

The incubation medium was then washed off and the cells were rinsed 3 times to remove any trace of bovine TIMP. The medium was then replaced with serum-free medium supplemented with $^{35}S$ methionine (New England Nuclear, Boston, Mass. having specific activity of 1000 Ci/mmol, or greater) resulting in a final $^{35}S$ concentration of 50 μCi/ml. The cells were incubated at 37° C. for 5 hours after which culture medium was collected and then stored at −70° C.

Secretion of TIMP-1

Secretion of TIMP-1 protein into the culture medium by the fibroblast cells was confirmed by immunoprecipitation and autoradiography as described below. To a 200 μl volume of the culture medium was added an 800 μl volume (0.8 ml) of 1X immunoprecipitation buffer (RIPA) that comprised 1% (w/v) deoxycholate, 0.1% sodium dodecylsulfate ("SDS"), 1.5% (w/v) Triton® X-100, Biorad, Richmond, Calif., and 10 mM Tris.Cl, pH 7.5. The mixture was then incubated for 1 hour at 4° C. with approximately 2 μl of a polyclonal antiserum to TIMP-1 (courtesy of Dr. G. Murphy, Strangeways Research Laboratories, Cambridge, UK) having a titer of greater than 1000. Alternatively, monoclonal or polyclonal antibodies to TIMP-1 can be made by well known processes that involve immunizing animals with TIMP-1, or with a peptide having substantial sequence homology therewith. A preferred reference manual of techniques for producing, screening and characterizing antibodies is Harlow, E., and Lane, D., eds. *Antibodies: A Laboratory Manual*, Cold Spring Harbor Laboratory Press, Cold Spring Harbor, N.Y. (1988). A preferred reference on the production of monoclonal antibodies is Harlow, E. and Lane, D., eds., supra, at pages 150–238 thereof. See also K öhler, et al., *Eur. J. Immunol.*, 6, 292–295 (1976). Use of a polyclonal antiserum for immunoprecipitation is preferred to assure highest yield of IgG/TIMP-1 complexes.

Immune complexes were precipitated by taking advantage of the affinity of protein A (isolated from the cell wall of *Staphylococcus aureus*) for constant regions of heavy chain antibody polypeptides, following generally the method of Cullen, B. et al., *Meth. Enzymology*, 152, 684–704 (1987). See also Harlow, E. and Lane, D., supra, at chapters 14–15 thereof.

Protein-A Sepharose®4B beads were purchased from Pharmacia, Uppsala, Sweden and used according to manufacturers instructions and well established procedures. Immune complexes prepared therewith were then pelleted in the presence of "RIPA" buffer and then washed three times therein.

Immunoprecipitated proteins were then electrophoresed in polyacrylamide gels containing SDS following the method of Weber, K. et al. *J. Biol. Chem.*, 244, 4406–4412 (1969), as modified by Laemli, U.K. *Nature*, 227, 680–685 (1970) using an acrylamide concentration of 11%. Samples of immuno-complexed TIMP-1 protein were dissociated prior to electrophoresis by heating at 100° C. for 5 minutes in 2% SDS-containing acrylamide gel sample buffer (with 700 mM β-mercaptoethanol, providing reducing conditions) to disrupt non-covalent bonds and disulfide bonds. The protein-A Sepharose® beads were spun down and discarded.

The gels were then dried and subjected to autoradiography (using Kodak X-OMAT, XAR 5 X-ray film) to develop the $^{35}S$ label. "Antigen" reacting with polyclonal TIMP-1 antiserum was detected in each gel sample lane, including the control lane (corresponding to medium from cells for which no aliquot of oncostatin-M was added). As can be seen in FIG. 1, increasing the concentration of oncostatin-M to which the cells were exposed (from 1 to 50 ng/ml) caused a substantial progressive increase in the amount of TIMP-1 that was secreted.

Example 2

Cytokine-enhanced Expression of TIMP-1 and Type-1 Collagenase Proteins

Following generally the procedures of Example 1, the effect of certain cytokines on TIMP-1 and type-1 collagenase expression from confluent cultures of human fibroblasts of normal lung tissue was determined. As in Example 1, confluent cultures were stimulated with a particular concentration of a recombinantly-produced cytokine for 18 hours in DMEM/2% FBS.

Separate aliquots of equivalent volume of culture supernatant were analyzed for TIMP-1 (FIG. 2—panel A) and type-1 collagenase (FIG. 2—panel B) by immunoprecipitation. Immunoreactive serum containing anti-type 1 collagenase polyclonal antibody was provided by Dr. G. Murphy, Strangeways Research Laboratories, Cambridge, United Kingdom. Such serum may be prepared readily according to standard procedures. Alternate techniques to assay collagenases were described above.

Cytokines were tested at single concentrations as follows: control ("C" in FIG. 2), O added cytokine/ml; oncostatin-M ("OM" in FIG. 2), 30 ng/ml; interleukin-6 ("IL-6" in FIG. 2), 50 ng/ml; leukemia inhibitory factor ("LIF" in FIG. 2), 5000 U/ml, where 1 U equals the inverse of the dilution that gave half-maximal response in supporting proliferation of the leukemia cell line DA-1a (Moreau et al. *Nature*, 336, 690–692 (1988)); and interleukin-1α ("IL-1α" in FIG. 2), 5 ng/ml. A stock solution of recombinant oncostatin-M was prepared as referred to in Example 1. Recombinant IL-6, LIF and IL-1α were prepared according to published procedures. Recombinant human interleukin-6 was expressed from yeast cells (and used as a dilution of the yeast supernatant in PBS), and was provided by Dr. S. Gillis, Immunex Corp., Seattle, Wash. Recombinant human leukemia inhibitory factor was expressed from CHO cells, according to published procedures, and applied as a dilution (about 1:20 to about 1:100 in phosphate buffered saline) of the cell culture supernatant (provided by Dr. G. Wong, Genetics Institute, Cambridge, Mass.). Recombinant human interleukin-1α (provided by Dr. J. Saklatvala, Strangeways Research Laboratories, Cambridge, U.K.) was expressed from *E. coli*, and purified by affinity chromatography. A stock solution thereof was diluted in PBS for use in the assays. Interleukin-6, leukemia inhibitory factor, and interleukin-1α are available also from commercial sources (for example, Genzyme Corp., Boston, Mass. for Il-1α AND IL-6, and Genetics Institute, Cambridge, Mass. for LIF).

Reference to FIG. 2 shows the levels of expression resultant from use of the specified concentrations of and species of cytokine. Each cytokine, used at the above-specified concentration, increased the yield of secreted TIMP-1 protein detectable in the culture medium immunoprecipitate. The effect on TIMP-1 secretion however was most pronounced when oncostatin-M (final concentration 30 ng/ml) was used. Use of oncostatin-M, interleukin-6 and also leukemia inhibitory factor at the above specified concentrations thereof had no effect on type-1 (pro)collagenase synthesis. However use of interleukin-1α decidedly increased production of the procollagenase even though TIMP-1 synthesis was also increased.

Example 3

Induction of Synthesis of TIMP-1 mRNA

In order to determine the effect of certain cytokines on synthesis of mRNA encoding TIMP-1, confluent cultures of human fibroblasts were prepared as in Example 1. The cells were then incubated at 37° C. in a 5% $CO_2$ atmosphere for 18 hours, again following the procedure of Example 1, with specific single dose final concentrations of the following cytokines: oncostatin-M, 50 ng/ml; interleukin-6, 50 ng/ml; leukemia inhibitory factor (5000 U/ml); and interleukin-1a (5 ng/ml).

RNA was extracted from the cultured cells following the method described in Chomczynski, P. and Sacchi, N. *Anal. Biochem.*, 162, 156–159 (1987). Briefly the method involves a single step phenol/chloroform extraction using guanidinium salts. Ten μg aliquots of purified RNA in sample buffer were then subjected to electrophoresis (for Northern hybridization) in formaldehyde/denaturing 1% agarose gels according to a standard procedure. The method follows generally the procedure described in *Molecular Cloning, A Laboratory Manual*, Sambrook, J., Fritsch, E. F., and Maniatis, T., Cold Spring Harbor Laboratory Press, Cold Spring Harbor, N.Y., 2nd ed. (1989), hereinafter ("Maniatis, T. et al., 1989") at page 7.43 thereof. Equivalence of the total RNA amount of each of the loaded samples was confirmed using ethidium bromide staining. The developed RNA gels were then transferred to a charged nylon membrane (Biotrans, ICN, Irvine, Calif.) following manufacturers instructions. See also, generally, Maniatis, T. et al., 1989 at page 9.34–9.37.

RNA was then quantified using probe cDNAs (themselves radiolabelled by the random primer technique using an oligo labelling kit, Pharmacia, Uppsala, Sweden and following manufacturers instructions) for TIMP-1, stromelysin, interleukin-6, and type-1 collagenase (panels A, B, C and D respectively in FIG. 3). The oligo labelling method was derived, generally, from the procedures of Feinberg and Vogelstein. See *Anal. Biochem.*, 132, 6 (1983), and *Anal. Biochem.*, 137, 266 (1984). Hybridization and autoradiography followed generally the procedure described by Maniatis, T. et al., 1989 at page 7.52. Samples of cDNA for human type-1 collagenase, human TIMP-1, and human stromelysin were a gift from A. J. P. Docherty (Celltech Ltd., Slough, UK). Samples of cDNA for human interleukin-6 were prepared by standard procedures.

Reference to FIG. 3 demonstrates that only interleukin-1α stimulated production of type-1 collagenase mRNA or stromelysin mRNA (panel C). Although IL-1α also stimulates TIMP-1 production (panel D), the combined stimulating effect may make it an unlikely therapeutic for degenerative or inflammatory disease or to inhibit invasive behavior of tumors. As shown in panel B of FIG. 3, IL-1α also stimulates production of IL-6 mRNA. In contrast, oncostatin-M stimulation of fibroblasts results in a pronounced effect on TIMP-1 mRNA expression (panel A, FIG. 3), and, importantly, no effect on steady state levels of stromelysin or type-1 collagenase MRNA production (panels C and D in FIG. 3).

Example 4

Figure 4:
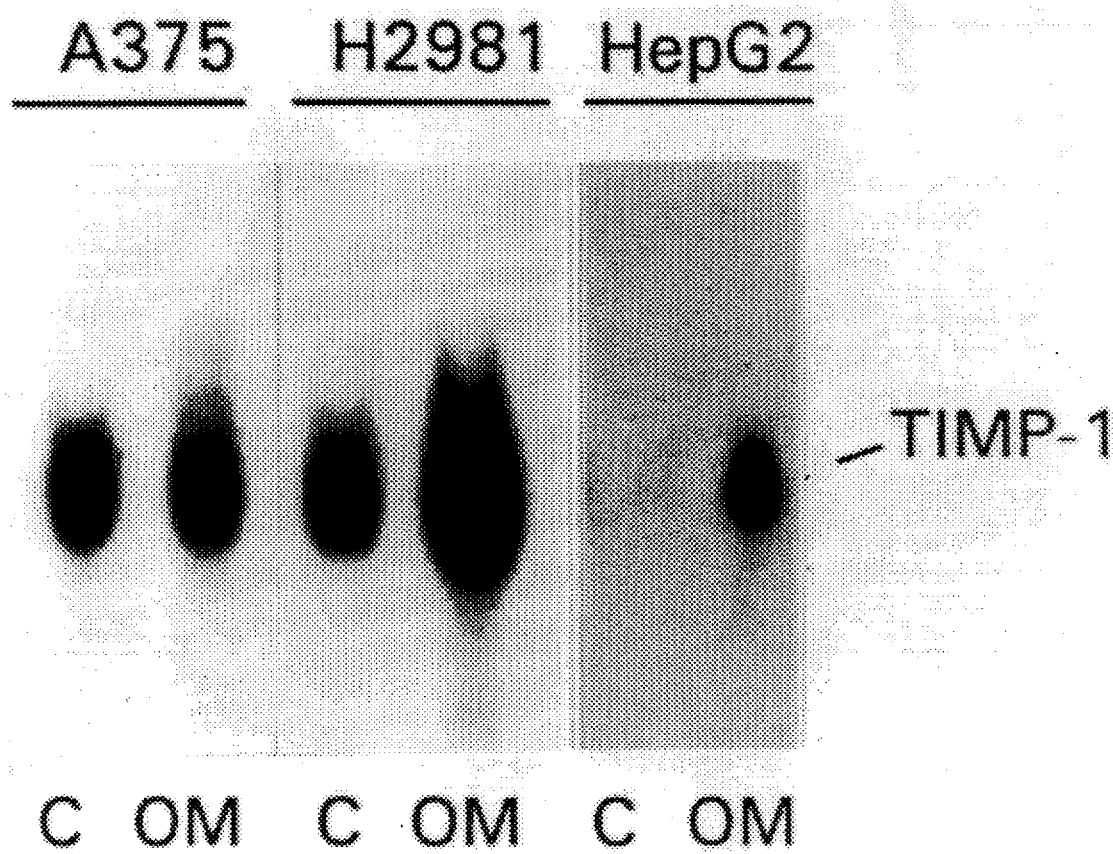
FIG. 4 is a northern blot that demonstrates stimulation of TIMP mRNA production in certain tumor cell lines.

Stimulation by Oncostatin-M of TIMP-1 Expression in Certain Tumor Cell Lines Confluent cultures of the following permanent (tumor) cell lines were prepared: A375 malignant melanoma cell line (ATCC CRL 1619) from the American Type Culture Collection, Rockville, Md., see Giard, D. J. et al. *J. Natl. Cancer Inst.*, 51, 1417–1423 (1973); H2981 lung carcinoma cell line provided by Dr. I. Hellstrom (see Hellstrom, I. et al. *Cancer Res.*, 46, 3917–3923 (1986)); and HepG2 cell line (ATCC HB 8065), human hepatoma, B. Knowles, Wistar Institute, Philadelphia, Pa. (see Knowles, B. et al. *Science*, 209, 497 (1980). DMEM/10% FBS growth medium was used for each of the cell lines. After confluence was achieved, the medium for samples of each cell line was replaced with DMEM/2% FBS and then maintained for 18 hours, with and without oncostatin-M at 50 ng/ml. Northern blots (using a procedure as modified by White, B. A. and Bancroft, F. C. *J. Biol. Chem.*, 257, 8569–8572 (1982)) were then probed with TIMP-1 cDNA. As demonstrated in FIG. 4, oncostatin-M increased TIMP-1 expression by cells of the HepG2 and H2981 tumor cell lines but not by the A375 cells. Growth of A375 melanoma cells is actually inhibited by oncostatin-M suggesting an altered oncostatin-M receptor or receptor response as mentioned above. Equivalence of RNA loading for the hybridizations was confirmed using intensity of ethidium bromide staining.

Example 5

Inhibition of Growth of a Malignant Tumor

Preliminary data have been acquired from the treatment of malignant tumors in mice with oncostatin-M. Based on this data and toxicity data obtained with mice and dogs, recommended doses of oncostatin-M for administration to humans to prevent or inhibit metastasis of tumors are predicted to be from about 0.05 to about 5 milligrams per patient per day with about 1 milligram per day per 70 kg patient being a representative preferred dose. It is believed also, based on toxicity studies in mice and/or dogs, that doses up to about 10 mg/day per 70 kg patient, or even higher, may not be toxic to humans. It is noted that under some circumstances oncostatin-M appears to be more toxic on a per kilogram basis in dogs than in mice. Such differences are commonly encountered with respect to administration of therapeutic doses to mammals. It is well within the routine of clinical practice to use such information in order to optimize therapeutic doses for humans.

For the purposes of treatment according to the above guidelines, patients could be selected, for example, who had been identified as having primary tumors with presence also of multiple metastasized masses. The patients would be administered standard chemotherapeutic agents in daily doses per accepted medical procedures. The patients would be administered also human oncostatin-M at a dose or doses within the above mentioned recommended ranges. It is expected that following such combined therapy, after a period of treatment of, for example, two to eight weeks that the metastatic potential of the tumor cell population will be reduced. Remaining tumor cells are expected to be eliminated following continued chemotherapy and continued provision of oncostatin-M.

Additionally, it is expected that other cytokines (such as macrophage activating factors) can be co-administered with oncostatin-M leading to the activation of other tumoricidal pathways.

Example 6

Application of Oncostatin-M to Arthritis-Affected Tissues

In vivo model systems are presently available to investigate arthritic disease states. For example, it has been demonstrated that Wistar rats, when immunized with native type II collagen (isolated from digestion of fetal bovine articular cartilage), develop arthritic disease as a result of collagen-immunity response. Such response is believed to be related to the progression of human rheumatoid arthritis. See Stuart, J. M. et al. *J. Exp. Med.*, 155, 1–16 (1982) and references cited therein. Other animal models include use of intradermal injection with complete Freunds adjuvant (see Chang et al. *Arth. Rheum.*, 23, 62–71 (1980)) and intraperitoneal injection of *Streptococcus* cell wall extracts in Lewis rats (see Wilder, et al. *Arth. Rheum.*, 25, 1064 (1982)).

Experimental animal models for the progression of osteoarthritis in humans have also been developed which reproduce the progressive histologic and biochemical changes of human osteoarthritic disease. See Pelletier, Jean-Pierre et al. *Arthritis and Rheumatism*, 26(7), 866–874 (1983) and also Pond, M. J. and Nuki, G. *Ann. Rheum. Dis.*, 32, 387–388 (1973), McDevitt, C. A. et al. *J. Bone Joint Surg.*, 59B, 24–35 (1977).

The results of these model studies and the discoveries of the present invention suggest that progression of arthritic disease in humans may be halted, or in fact reversed, using subcutaneous or intraarticular injections of human oncostatin-M, at about 1 to about 50 µg/ml in saline buffer using an injection volume compatible with the volume of the affected site, for example, about 0.1 ml per 10 ml of inflamed synovial fluid, said administration being made on a daily basis for a period of about 1 to about 30 days.

It is expected that improvement will be demonstrated within this period following such daily administrations at which time the injections may be discontinued. If further healing does not occur, a second course of administrations would be indicated.

Example 7

Treatment of Erythrocytic Anemia

As described above, oncostatin-M has utility in the treatment of diseases or conditions involving a deficiency of red blood cells. It is expected that intravenous administration of oncostatin-M to achieve a dose of about 0.05 to about 5.0 mg/per patient per day results in a steady-state level of TIMP-1 sufficient to enhance substantially the rate at which erythroid-committed stem cells further differentiate and proliferate. Alternatively, oncostatin-M can be injected into the bone marrow. Administration of appropriate levels of oncostatin-M for a period of about 1 to about 10 weeks is predicted to be sufficient to return red blood cell counts in patients to normal levels for many disease states. Such stimulatory effects of oncostatin-M on cells of red cell lineage occur through mediation by TIMP and are likely to occur also by direct action of oncostatin-M on the target erythropoetic cells.

Example 8

Stimulation of TIMP-1 Secretion by Bone Marrow Stromal Cells

This Example demonstrates that the amount of TIMP-1 protein secreted in vitro by human bone marrow stromal cells is upregulated by oncostatin-M.

Human bone marrow samples were obtained from healthy donors following informed consent and research center guidelines at the Fred Hutchison Cancer Research Center, Seattle, Wash. Cells were separated by density gradient centrifugation, Andrews, R. G. et al. *J. Exp. Med.*, 169, 1721 (1989). Adherent marrow-stromal cells were separated from nonadherent colony forming cells according to established procedures by overnight incubation on plastic culture dishes, followed by washing with Iscove's Modified Dulbecco's Medium ("IMDM") supplied by Gibco/Life Technologies, Inc., Gaithersburg, Md.

Adherent marrow-stromal cells were maintained in culture for 30 days with LTCM (long term culture medium, comprising IMDM, 1 micromolar hydrocortisone, 0.1 MMB-mercaptoethanol vitamins and essential and non-essential amino acids supplemented with 20% heat-inactivated fetal bovine serum (Hyclone Co., Logan, Utah) and with 12.5% non-heat inactivated horse serum (Gibco/Life Technologies, Inc. The growth medium was then replaced with serum-free Hybridoma Medium (Gibco/Life Technologies, Inc.) containing also 2% LTCM and the cells were maintained therein for 24 hours. Oncostatin-M (to achieve the final concentrations thereof specified below) was added to the incubation medium and remained in contact with the cells for 18 hours. The adherent cells were then washed twice with phosphate buffered saline and then cultured (for 6 hours) in methionine/cysteine-free Minimal Essential Medium (Gibco/Life Technologies, Inc.) containing 2% heat-inactivated fetal bovine serum and also 150 µCi/ml of $^{35}$S-methionine (from Amersham). Media samples were then harvested and analyzed for TIMP-1 content following the immunoprecipitation, electrophoresis and autoradiography procedures of Example 1.

Results were determined by measuring the intensity of the 28,000 molecular weight bands of the developed autoradiogram using laser-enhanced densitometry (LKB Ultrascan XL model densitometer). Analysis of the autoradiogram provided the following results (measuring absorbance units/mm for the 28 kDa bands): for the oncostatin-M untreated control, 0.18; with oncostatin-M at 0.1 ng/ml, 0.21; with oncostatin-M at 1 ng/ml, 0.30; and with oncostatin-M at 100 ng/ml, 0.38.

We claim:

1. A method for promoting healing of an injury in a patient comprising administering to said patient a tissue inhibitor of metalloproteinase (TIMP) increasing effective amount of a therapeutic composition comprising oncostatin-M.

2. A method for regulating tissue remodeling in a patient in need thereof comprising administering to said patient a tissue inhibitor of metallo proteinase (TIMP) increasing effective amount of a therapeutic composition comprising oncostatin-M.

3. A method for stimulating erythropoiesis in a patient that comprises the step of administering to said tissue a tissue inhibitor of metalloproteinase (TIMP) increasing effective amount of the cytokine oncostatin-M.

4. A method of stimulating erythroid-committed stem cells that are in contact with bone marrow stromal cells to further differentiate or proliferate, comprising the step of contacting said stromal cells with a tissue inhibitor of metalloproteinase (TIMP) increasing effective amount of the cytokine oncostatin-M, wherein secretion by said stromal cells of TIMP is increased relative to a predetermined value thereof and said TIMP is available to said stem cells and increases the differentiation or proliferation thereof.

5. A method for producing tissue inhibitor of metalloproteinase (TIMP) comprising the steps of (1) culturing mammalian cells; (2) contacting said cultured cells with a TIMP increasing effective amount of oncostatin-M; and (3) collecting the TIMP from the cells in step (2).

* * * * *

UNITED STATES PATENT AND TRADEMARK OFFICE
CERTIFICATE OF CORRECTION

PATENT NO. : 5,744,442  
DATED : April 28, 1998  
INVENTOR(S) : Carl L RICHARDS, et al.

Page 1 of 3

It is certified that error appears in the above-identified patent and that said Letters Patent is hereby corrected as shown below:

Column 4, line 46, change "LIMP") to --"LIMP.").

Column 5, line 44, change "efficiency" to --deficiency--.

Column 7, line 31, change "secret ion" to --secretion--.

Column 7, line 54, change "MRNA" to --mRNA--.

Column 7, line 55, change "MRNA" to --mRNA--.

Column 9, line 3, change "CDNA" to --cDNA--.

Column 19, line 29, change "$a_2M$-," to --$d_2M$-,--.

Column 22, line 3, under "Nature," and type in italics.

Column 24, line 64, change "Rest." to --Resp.--.

Column 25, line 51, delete "K" at end of line.

Column 25, line 52, change "ohler," to --Kohler--.

Column 27, line 28, change "interleukin-1a" to --interleukin-1d--.

UNITED STATES PATENT AND TRADEMARK OFFICE
CERTIFICATE OF CORRECTION

PATENT NO. : 5,744,442
DATED : April 28, 1998
INVENTOR(S) : Carl I. RICHARDS, et al.

It is certified that error appears in the above-identified patent and that said Letters Patent is hereby corrected as shown below:

Column 28, line 9, change "MRNA" to --mRNA--.

Column 30, line 30, change "MMB-mercaptoethanol" to --mM B-mercaptoethanol--.

Column 30, line 31, change "acids" to --acids)-- and change "20%" to --12.5%--.

Column 30, line 32, after "Utah)" insert a comma.

Column 30, line 34, change "Inc." to --Inc.)--.

Column 30, line 36, after "LTCM" insert a comma.

Column 30, line 45, leave a space between "of" and "$^{35}S$.".

Column 30, line 65, change "metallo proteinase" to --metalloproteinase--.

UNITED STATES PATENT AND TRADEMARK OFFICE
CERTIFICATE OF CORRECTION

PATENT NO.  : 5,744,442
DATED       : April 28, 1998
INVENTOR(S) : Carl I. RICHARDS, et al.

It is certified that error appears in the above-identified patent and that said Letters Patent is hereby corrected as shown below:

Column 31, line 2, change "said tissue" to --said patient--.

Signed and Sealed this

Fifth Day of January, 1999

Attest:

Attesting Officer

Acting Commissioner of Patents and Trademarks